US012784873B2

(12) United States Patent
Hamp et al.

(10) Patent No.: US 12,784,873 B2
(45) Date of Patent: Nov. 3, 2026

(54) SPECIES PROXIMITY-AWARE EVOLUTIONARY CONSERVATION PROFILES

(71) Applicant: Illumina, Inc., San Diego, CA (US)

(72) Inventors: Tobias Hamp, Cambridge (GB); Kai-How Farh, Hillsborough, CA (US)

(73) Assignee: Illumina, Inc., San Diego, CA (US)

(*) Notice: Subject to any disclaimer, the term of this patent is extended or adjusted under 35 U.S.C. 154(b) by 951 days.

(21) Appl. No.: 17/975,563

(22) Filed: Oct. 27, 2022

(65) Prior Publication Data

US 2023/0207047 A1 Jun. 29, 2023

Related U.S. Application Data

(60) Provisional application No. 63/294,813, filed on Dec. 29, 2021, provisional application No. 63/294,820, (Continued)

(51) Int. Cl.
*G16B 30/00* (2019.01)
*G06F 18/2111* (2023.01)
(Continued)

(52) U.S. Cl.
CPC .......... *G16B 30/00* (2019.02); *G06F 18/2111* (2023.01); *G06F 18/2148* (2023.01); (Continued)

(58) Field of Classification Search
CPC ............. G06F 18/2111; G06F 18/2148; G06F 18/2155; G06N 20/00; G06N 20/20; G06N 3/044; G06N 3/045; G06N 3/0464; G06N 3/047; G06N 3/08; G06N 3/084; G06N 3/126; G06B 10/00; G06B 20/00; G06B 20/20; G06B 20/40; G06B 30/00;
(Continued)

(56) References Cited

U.S. PATENT DOCUMENTS 5,869,036 A 2/1999 Belshe et al.
6,110,457 A 8/2000 Belshe et al.
(Continued)

FOREIGN PATENT DOCUMENTS

AU 2011203297 A1 7/2011
CA 3066775 A1 4/2019
(Continued)

OTHER PUBLICATIONS

Ma, Wenlong, et al. "A deep convolutional neural network approach for predicting phenotypes from genotypes." Planta 248.5 (2018): 1307-1318. (Year: 2018).*
(Continued)

*Primary Examiner* — Andrew L Tank
(74) *Attorney, Agent, or Firm* — Keller Preece PLLC

(57) ABSTRACT

The technology disclosed relates to generating species-differentiable evolutionary profiles using a weighting logic. In particular, the technology disclosed relates to determining a weighted summary statistic for a given residue category at a given position in a multiple sequence alignment based on one or more weights of one or more sequences in the multiple sequence alignment that have a residue of the given residue category at the given position.

26 Claims, 13 Drawing Sheets

Related U.S. Application Data filed on Dec. 29, 2021, provisional application No. 63/294,816, filed on Dec. 29, 2021, provisional application No. 63/294,830, filed on Dec. 29, 2021, provisional application No. 63/294,827, filed on Dec. 29, 2021, provisional application No. 63/294,828, filed on Dec. 29, 2021.

(51) Int. Cl.

| | |
|---|---|
| ***G06F 18/214*** | (2023.01) |
| ***G06N 3/045*** | (2023.01) |
| ***G06N 3/0464*** | (2023.01) |
| ***G06N 3/08*** | (2023.01) |
| ***G06N 3/126*** | (2023.01) |
| ***G06N 20/00*** | (2019.01) |
| ***G06N 20/20*** | (2019.01) |
| ***G16B 10/00*** | (2019.01) |
| ***G16B 20/00*** | (2019.01) |
| ***G16B 20/20*** | (2019.01) |
| ***G16B 20/40*** | (2019.01) |
| ***G16B 30/10*** | (2019.01) |
| ***G16B 40/00*** | (2019.01) |
| ***G16B 40/20*** | (2019.01) |
| ***G16B 40/30*** | (2019.01) |
| ***G16B 50/10*** | (2019.01) |

(52) U.S. Cl.

CPC ......... *G06F 18/2155* (2023.01); *G06N 3/045* (2023.01); *G06N 3/0464* (2023.01); *G06N 3/08* (2013.01); *G06N 3/126* (2013.01); *G06N 20/00* (2019.01); *G06N 20/20* (2019.01); *G16B 10/00* (2019.02); *G16B 20/00* (2019.02); *G16B 20/20* (2019.02); *G16B 20/40* (2019.02); *G16B 30/10* (2019.02); *G16B 40/00* (2019.02); *G16B 40/20* (2019.02); *G16B 40/30* (2019.02); *G16B 50/10* (2019.02)

(58) Field of Classification Search

CPC ........ G06B 30/10; G06B 40/00; G06B 40/20; G06B 40/30; G06B 50/10; Y02A 90/10

See application file for complete search history.

(56) References Cited

U.S. PATENT DOCUMENTS

| | | | | |
|---|---|---|---|---|
| 10,354,747 | B1 | 7/2019 | Depristo et al. | |
| 2007/0071720 | A1 | 3/2007 | Janssen et al. | |
| 2007/0298503 | A1 | 12/2007 | Lathrop et al. | |
| 2013/0268290 | A1 | 10/2013 | Jackson et al. | |
| 2014/0302042 | A1 | 10/2014 | Chin et al. | |
| 2015/0261913 | A1* | 9/2015 | Dewey | G16B 30/00 702/19 |
| 2015/0363546 | A1 | 12/2015 | Delaney et al. | |
| 2016/0253452 | A1 | 9/2016 | Karbassi et al. | |
| 2017/0220734 | A1 | 8/2017 | Colavin et al. | |
| 2017/0316149 | A1 | 11/2017 | Maston et al. | |
| 2018/0218116 | A1 | 8/2018 | Agrawal et al. | |
| 2018/0300450 | A1 | 10/2018 | Hogan et al. | |
| 2019/0073445 | A1 | 3/2019 | Shen et al. | |
| 2019/0114544 | A1* | 4/2019 | Sundaram | G06F 18/24 |
| 2019/0172550 | A1 | 6/2019 | Ghosh | |
| 2019/0220740 | A1* | 7/2019 | Xiong | G06N 3/0464 |
| 2019/0266493 | A1* | 8/2019 | Gao | G06N 3/08 |
| 2019/0318806 | A1 | 10/2019 | Wise et al. | |
| 2019/0359990 | A1 | 11/2019 | Tuller et al. | |
| 2020/0020416 | A1 | 1/2020 | Artieri et al. | |
| 2020/0097835 | A1 | 3/2020 | Silver et al. | |
| 2020/0265922 | A1 | 8/2020 | Rabizadeh et al. | |
| 2020/0273541 | A1* | 8/2020 | Costello | G16B 50/00 |
| 2021/0065844 | A1* | 3/2021 | Merril | G06N 20/00 |
| 2021/0074378 | A1 | 3/2021 | Zhou et al. | |
| 2021/0102197 | A1* | 4/2021 | Sabeti | G16B 40/20 |
| 2021/0343372 | A1 | 11/2021 | Tell et al. | |
| 2022/0056502 | A1 | 2/2022 | Li et al. | |
| 2022/0084631 | A1 | 3/2022 | Ju et al. | |
| 2022/0230764 | A1* | 7/2022 | Lee | G16B 15/20 |
| 2022/0348903 | A1* | 11/2022 | Ranganathan | G16B 25/10 |
| 2023/0068937 | A1 | 3/2023 | Morganella et al. | |
| 2023/0154561 | A1* | 5/2023 | Cheng | G06N 3/084 702/19 |
| 2023/0162004 | A1* | 5/2023 | Pan | G06N 3/045 702/1 |
| 2023/0207058 | A1 | 6/2023 | Gao et al. | |
| 2024/0371528 | A1 | 11/2024 | Maher et al. | |

FOREIGN PATENT DOCUMENTS

| | | | |
|---|---|---|---|
| WO | 2012-034030 | A1 | 3/2012 |
| WO | 2013/067001 | A1 | 5/2013 |
| WO | 2019/079180 | A1 | 4/2019 |
| WO | 2020/167667 | A1 | 8/2020 |
| WO | 2021/050923 | A1 | 3/2021 |
| WO | 2021-077163 | A1 | 4/2021 |
| WO | 2023/014913 | A1 | 2/2023 |
| WO | 2023/129621 | A1 | 7/2023 |
| WO | 2024/079204 | A1 | 4/2024 |

OTHER PUBLICATIONS

Aoki, Genta, and Yasubumi Sakakibara. “Convolutional neural networks for classification of alignments of non-coding RNA sequences.” Bioinformatics 34.13 (2018): i237-i244. (Year: 2018).*

Ali, Raja Hashim, Marcin Bogusz, and Simon Whelan. “Identifying clusters of high confidence homologies in multiple sequence alignments.” Molecular biology and evolution 36.10 (2019): 2340-2351. (Year: 2019).*

Jaganathan, Kishore, et al. “Predicting splicing from primary sequence with deep learning.” Cell 176.3 (2019): 535-548. (Year: 2019).*

Liu, Yang, et al. “Phenotype prediction and genome-wide association study using deep convolutional neural network of soybean.” Frontiers in genetics 10 (2019): 1091. (Year: 2019).*

Forghani, Majid, and Michael Khachay. “Convolutional neural network based approach to in silico non-anticipating prediction of antigenic distance for influenza virus.” Viruses 12.9 (2020): 1019. (Year: 2020).*

Iqbal, Sumaiya, et al. “Comprehensive characterization of amino acid positions in protein structures reveals molecular effect of missense variants.” Proceedings of the National Academy of Sciences 117.45 (2020): 28201-28211. (Year: 2020).*

Malhis, Nawar, et al. “LIST-S2: taxonomy based sorting of deleterious missense mutations across species.” Nucleic acids research 48.W1 (2020): W154-W161, including corresponding Supplementary Data. (Year: 2020).*

Muntoni, Anna Paola, et al. “Aligning biological sequences by exploiting residue conservation and coevolution.” Physical Review E 102.6 (2020): 062409. (Year: 2020).*

Jing, Bowen, et al. “Learning from protein structure with geometric vector perceptrons.” arXiv preprint arXiv:2009.01411 (2020). (Year: 2020).*

Pei, Jimin, and Nick V. Grishin. “The DBSAV database: predicting deleteriousness of single amino acid variations in the human proteome.” Journal of molecular biology 433.11 (2021): 166915 (Year: 2021).*

Pei, Jimin, et al. “Mutation severity spectrum of rare alleles in the human genome is predictive of disease type.” PLoS computational biology 16.5 (2020): e1007775 (Year: 2020).*

H. Gao et al. “The landscape of tolerated genetic variation in human and primates”, Science 380, eabn8197 (2023) DOI: 10.1126/science.abn8197.

Pollard Katherine S. et al: “Detection of nonneutral substitution rates on mammalian phylogenies”, Genome Research, vol. 20, No. 1, Oct. 26, 2009 (Oct. 26, 2009), pp. 110-121, XP093111876, us ISSN: 1088-9051, DOI: 10.1101/gr.097857.109.

A. B. Rylands, R. A. Mittermeier, Primate Behavioral Ecology. (Routledge, New York, ed. 6, 2021), pp. 407-428.

(56) References Cited

OTHER PUBLICATIONS

A. Bentivegna et al., Rubinstein-Taybi Syndrome: spectrum of CREBBP mutations in Italian patients. BMC Med Genet 7, 77 (2006).
A. Estrada et al., Impending extinction crisis of the world's primates: Why primates matter. Sci. Adv 3, e1600946 (2017).
A. Eyre-Walker, P. D. Keightley, The distribution of fitness effects of new mutations. Nature Reviews Genetics 8, 610-618 (2007).
A. J. Riesselman, J. B. Ingraham, D. S. Marks, Deep generative models of genetic variation capture the effects of mutations. Nat Methods 15, 816-822 (2018).
A. O. Giacomelli et al., Mutational processes shape the landscape of TP53 mutations in human cancer. Nature Genetics 50, 1381-1387 (2018).
A. R. Martin et al., PanelApp crowdsources expert knowledge to establish consensus diagnostic gene panels. Nat Genet 51, 1560-1565 (2019).
A. Sali, T. L. Blundell, Comparative protein modelling by satisfaction of spatial restraints. J Mol Biol 234, 779-815 (1993).
A. S. Kondrashov, S. Sunyaev, F. A. Kondrashov, Dobzhansky-Muller incompatibilities in protein evolution. Proc. Natl. Acad. Sci. U.S.A.99, 14878-14883 (2002).
A. Thormann et al., Flexible and scalable diagnostic filtering of genomic variants using G2P with Ensembl VEP. Nat Commun 10, 2373 (2019).
B. E. Suzek, H. Huang, P. McGarvey, R. Mazumder, C. H. Wu, UniRef: comprehensive and non-redundant UniProt reference clusters. Bioinformatics 23, 1282-1288 (2007).
B. E. Suzek, Y. Wang, H. Huang, P. B. McGarvey, C. H. Wu, UniRef clusters: a comprehensive and scalable alternative for improving sequence similarity searches. Bioinformatics (Oxford, England) 31, 926-932 (2015).
B. Heidenreich, R. Kumar, TERT promoter mutations in telomere biology. Mutation Research/Reviews in Mutation Research 771, 15-31 (2017).
B. J. Evans et al., Speciation over the edge: gene flow among non-human primate species across a formidable biogeographic barrier. R Soc Open Sci. 4, 170351 (2017).
B. J. O'Roak et al., Sporadic autism exomes reveal a highly interconnected protein network of de novo mutations. Nature 485, 246-250 (2012).
B.-J. Feng, PERCH: A Unified Framework for Disease Gene Prioritization. Human Mutation 38, 243-251 (2017).
B. Quintáns, A. Ordóñez-Ugalde, P. Cacheiro, A. Carracedo, M. J. Sobrido, Medical genomics: The intricate path from genetic variant identification to clinical interpretation. Appl. Transl. Genomics3, 60-67 (2014).
C. A. Cassa et al., Estimating the selective effects of heterozygous protein-truncating variants from human exome data. Nat Genet 49, 806-810 (2017).
C. Bycroft et al., The UK Biobank resource with deep phenotyping and genomic data. Nature 562, 203-209 (2018).
C. D. Bustamante, J. Wakeley, S. Sawyer, D. L. Hartl, Directional selection and the site-frequency spectrum. Genetics 159, 1779-1788 (2001).
C. E. G. Amorim, Z. Gao, Z. Baker, J. F. Diesel, Y. B. Simons, I. S. Haque, J. Pickrell, M. Przeworski, The population genetics of human disease: The case of recessive, lethal mutations. PLOS Genet.13, e1006915 (2017).
C. L. Araya et al., A fundamental protein property, thermodynamic stability, revealed solely from large-scale measurements of protein function. Proceedings of the National Academy of Sciences 109, 16858-16863 (2012).
C. Nakanishi et al., Germline mutation of the LKB1/STK11 gene with loss of the normal allele in an aggressive breast cancer of Peutz-Jeghers syndrome. Oncology 67, 476-479 (2004).
C. S. A. Consortium, Initial sequence of the chimpanzee genome and comparison with the human genome. Nature 437, 69-87 (2005).
C. Sudlow et al., UK biobank: an open access resource for identifying the causes of a wide range of complex diseases of middle and old age. PLoS Med 12, e1001779 (2015).
C. Tyner et al., The UCSC Genome Browser database: 2017 update. Nucleic Acids Res 45, D626-D634 (2017).
C. Zoonomia, A comparative genomics multitool for scientific discovery and conservation. Nature 587, 240-245 (2020).
D. Bates, M. Mächler, B. Bolker, S. Walker, Fitting Linear Mixed-Effects Models Using Ime4. Journal of Statistical Software, 67, 1-48 (2015).
D. E. Reich, E. S. Lander, On the allelic spectrum of human disease. Trends Genet 17, 502-510 (2001).
D. G. MacArthur et al., Guidelines for investigating causality of sequence variants in human disease. Nature 508, 469-476 (2014).
D. Hendrycks, K. Gimpel, Gaussian Error Linear Units (GELUs). arXiv:1606.08415 [cs.LG] (2020).
D. J. Burgess, The TOPMed genomic resource for human health. Nat Rev Genet 22, 200 (2021).
D. Kingma, J. Ba, Adam: A method for stochastic optimization. arXiv:1412.6980 [cs.LG] (2007).
D. M. Jordan, S. G. Frangakis, C. Golzio, C. A. Cassa, J. Kurtzberg, E. E. Davis, S. R. Sunyaev, N. Katsanis; Task Force for Neonatal Genomics, Identification of cis-suppression of human disease mutations by comparative genomics. Nature524, 225-229 (2015).
D. Quang, Y. Chen, X. Xie, DANN: a deep learning approach for annotating the pathogenicity of genetic variants. Bioinformatics 31, 761-763 (2015).
D. Raimondi et al., DEOGEN2: prediction and interactive visualization of single amino acid variant deleteriousness in human proteins. Nucleic Acids Research 45, W201-W206 (2017).
D. S. Marks, L. J. Colwell, R. Sheridan, T. A. Hopf, A. Pagnani, R. Zecchina, C. Sander, Protein 3D structure computed from evolutionary sequence variation. PLOS ONE6, e28766 (2011).
D. Taliun et al., Sequencing of 53,831 diverse genomes from the NHLBI TOPMed Program. Nature 590, 290-299 (2021).
D. Vanderpool et al., Primate phylogenomics uncovers multiple rapid radiations and ancient interspecific introgression. PLoS Biol 18, e3000954 (2020).
Deciphering Developmental Disorders Study, Large-scale discovery of novel genetic causes of developmental disorders. Nature 519, 223-228 (2015).
Deciphering Developmental Disorders Study, Prevalence and architecture of de novo mutations in developmental disorders. Nature 542, 433-438 (2017).
Dissertation et al: "Advanced Strategies for Alignment-based Real-time Analysis and Data Protection in Next-Generation Sequencing", Jan. 1, 2019 (Jan. 1, 2019), XP055870509, Retrieved from the Internet: URL: https://refubium.fu-berlin.de/bitstream/handle/fub188/26717/Dissertation_Loka.pdf?sequence=3&isAllowed=y [retrieved on Dec. 8, 2021].
Du Yuxuan et al: "HiCBin: binning metagenomic contigs and recovering metagenome-assembled genomes using Hi-C contact maps", Genome Biology, vol. 23, No. 1, Jan. 2, 2022 (Jan. 2, 2022), XP093055152, DOI: 10.1186/s13059-022-02626-w Retrieved from the Internet: URL: https://genomebiology.biomedcentral.com/counter/pdf/10.1186/s13059-022-02626-w.pdf.
E. M. Jones et al., Structural and functional characterization of G protein—coupled receptors with deep mutational scanning. eLife 9, e54895 (2020).
E. M. Leffler et al., Revisiting an old riddle: what determines genetic diversity levels within species? PLoS Biol 10, e1001388 (2012).
E. M. Leffler, Z. Gao, S. Pfeifer, L. Ségurel, A. Auton, O. Venn, R. Bowden, R. Bontrop, J. D. Wall, G. Sella, P. Donnelly, G. McVean, M. Przeworski, Multiple instances of ancient balancing selection shared between humans and chimpanzees. Science339, 1578-1582 (2013).
G. B. Pier et al., *Salmonella typhi* uses CFTR to enter intestinal epithelial cells. Nature 393, 79-82 (1998).
Gao Fei et al: "Direct ChIP-bisulfite sequencing reveals a role of H3K27me3 mediating aberrant hypermethylation of promoter CpG islands in cancer cells", Genomics, vol. 103, No. 2, pp. 204-210, XP028847145, ISSN: 0888-7543, DOI: 10.1016/J.YGENO.2013.12.006.

(56) References Cited

OTHER PUBLICATIONS

H. A. Shihab et al., An integrative approach to predicting the functional effects of non-coding and coding sequence variation. Bioinformatics 31, 1536-1543 (2015).
H. Carter, C. Douville, P. D. Stenson, D. N. Cooper, R. Karchin, Identifying Mendelian disease genes with the variant effect scoring tool. BMC Genomics14, S3 (2013).
H. D. Chae, C. H. Jeon, Peutz-Jeghers syndrome with germline mutation of STK11. Ann Surg Treat Res 86, 325-330 (2014).
H. L. Rehm et al., ClinGen—the Clinical Genome Resource. N Engl J Med 372, 2235-2242 (2015).
H. L. Rehm, Evolving health care through personal genomics. Nat Rev Genet 18, 259-267 (2017).
H. R. Yang, J. S. Ko, J. K. Seo, Germline mutation analysis of STK11 gene using direct sequencing and multiplex ligation-dependent probe amplification assay in Korean children with Peutz-Jeghers syndrome. Dig Dis Sci 55, 3458-3465 (2010).
H. Shu et al., The role of CD36 in cardiovascular disease. Cardiovascular Research, (2020).
Hemang Parikh et al: "svclassify: a method to establish benchmark structural variant calls", BMC Genomics, Biomed Central Ltd, London, UK, vol. 17, No. 1, Jan. 16, 2016 (Jan. 16, 2016), pp. 1-16, XP021233233, DOI: 10.1186/S12864-016-2366-2.
Henikoff S et al: "Position-based sequence weights", Journal of Molecular Biology, Academic Press, United Kingdom, vol. 243, No. 4, Nov. 4, 1994 (Nov. 4, 1994), pp. 574-578, XP024011362, ISSN: 0022-2836, DOI: 10.1016/0022-2836(94)90032-9 [retrieved on Nov. 4, 1994].
Hopf Thomas et al: "Mutation effects predicted from sequence co-variation", Nature Biotechnology, vol. 35, No. 2, Jan. 16, 2017, pp. 128-135, XP093038943, New York ISSN: 1087-0156, DOI: 10.1038/nbt.3769, Retrieved from the Internet: URL http://www.nature.com/articles/nbt3769>.
I. A. Adzhubei et al., A method and server for predicting damaging missense mutations. Nature Methods 7, 248-249 (2010).
I. Hernan et al., De novo germline mutation in the serine-threonine kinase STK11/LKB1 gene associated with Peutz-Jeghers syndrome. Clin Genet 66, 58-62 (2004).
I. Iossifov et al., De novo gene disruptions in children on the autistic spectrum. Neuron 74, 285-299 (2012).
I. Iossifov et al., The contribution of de novo coding mutations to autism spectrum disorder. Nature 515, 216-221 (2014).
I. Mathieson, G. McVean, Demography and the age of rare variants. PLOS Genet.10, e1004528 (2014).
J. A. SoRelle, D. M. Thodeson, S. Arnold, G. Gotway, J. Y. Park, Clinical Utility of Reinterpreting Previously Reported Genomic Epilepsy Test Results for Pediatric Patients. JAMA Pediatr 173, e182302 (2019).
J. Devlin, M.-W. Chang, K. Lee, K. Toutanova, BERT: Pre-training of Deep Bidirectional Transformers for Language Understanding. Proceedings of the 2019 Conference of the North American Chapter of the Association for Computational Linguistics: Human Language Technologies, vol. 1 (Long and Short Papers) (Association for Computational Linguistics, 2019). pp. 4171-4186 (2019).
J. E. Common, W.-L. Di, D. Davies, D. P. Kelsell, Further evidence for heterozygote advantage of GJB2 deafness mutations: a link with cell survival. Journal of medical genetics 41, 573-575 (2004).
J. Frazer et al., Disease variant prediction with deep generative models of evolutionary data. Nature 599, 91-95 (2021).
J. Jouganous, W. Long, A. P. Ragsdale, S. Gravel, Inferring the Joint Demographic History of Multiple Populations: Beyond the Diffusion Approximation. Genetics 206, 1549-1567 (2017).
J. Jumper et al., Highly accurate protein structure prediction with AlphaFold. Nature 596, 583-589 (2021).
J. Kaplanis et al., Evidence for 28 genetic disorders discovered by combining healthcare and research data. Nature 586, 757-762 (2020).
J. L. Ba, J. R. Kiros, G. E. Hinton, paper presented at the Advances in NIPS 2016 Deep Learning Symposium, Barcelona, Spain, Dec. 8, 2016.
J. L. Bobadilla, M. Macek Jr, J. P. Fine, P. M. Farrell, Cystic fibrosis: a worldwide analysis of CFTR mutations—correlation with incidence data and application to screening. Human mutation 19, 575-606 (2002).
J. Liu et al., Distribution of CD36 deficiency in different Chinese ethnic groups. Human Immunology 81, 366-371 (2020).
J. Meier et al., Language models enable zero-shot prediction of the effects of mutations on protein function. 2021.07.09.450648 [Preprint] (2021).
J. Prado-Martinez et al., Great ape genome diversity and population history. Nature 499, 471-475 (2013).
J. Söding, A. Biegert, A. N. Lupas, The HHpred interactive server for protein homology detection and structure prediction. Nucleic Acids Research 33, W244-W248 (2005).
J. Weile et al., A framework for exhaustively mapping functional missense variants. Mol Syst Biol 13, 957 (2017).
J. Y. An et al., Genome-wide de novo risk score implicates promoter variation in autism spectrum disorder. Science 362, (2018).
J. Yang et al., Improved protein structure prediction using predicted interresidue orientations. Proc Natl Acad Sci U S A 117, 1496-1503 (2020).
Jing Yu et al: "Detection of EP300-ZNF384 fusion in patients with acute lymphoblastic leukemia using RNA fusion gene panel sequencing", Annals of Hematology, Berlin, DE, vol. 99, No. 11, Sep. 26, 2020 (Sep. 26, 2020), pp. 2611-2617, XP037261202, ISSN: 0939-5555, DOI 10.1007 /S00277-020-04251-8 [retrieved on Sep. 26, 2020].
K. A. Jagadeesh et al., M-CAP eliminates a majority of variants of uncertain significance in clinical exomes at high sensitivity. Nature Genetics 48, 1581-1586 (2016).
K. A. Matreyek et al., Multiplex assessment of protein variant abundance by massively parallel sequencing. Nature Genetics 50, 874-882 (2018).
K. E. Eilertson, J. G. Booth, C. D. Bustamante, SnIPRE: Selection Inference Using a Poisson Random Effects Model. PLoS Comput Biol 8, e1002806 (2012).
K. E. Samocha et al., A framework for the interpretation of de novo mutation in human disease. Nat Genet 46, 944-950 (2014).
K. J. Karczewski et al., The mutational constraint spectrum quantified from variation in 141,456 humans. Nature 581, 434-443 (2020).
K. Reinson et al., Biallelic CACNA1A mutations cause early onset epileptic encephalopathy with progressive cerebral, cerebellar, and optic nerve atrophy. Am J Med Genet A 170, 2173-2176 (2016).
Kuck Patrick et al: "Parametric and non-parametric masking of randomness in sequence alignments can be improved and leads to better resolved trees", Frontiers in Zoology, Open Access Methodology, vol. 7, No. 10, Jan. 1, 2010, XP093043895, Retrieved from the Internet: URL: https://frontiersinzoology.biomedcentral.com/articles/10.1186/1742-9994-7-10 [retrieved on May 3, 2023].
L. Brenan et al., Phenotypic Characterization of a Comprehensive Set of MAPK1/ERK2 Missense Mutants. Cell Rep 17, 1171-1183 (2016).
L. Damaj et al., CACNA1A haploinsufficiency causes cognitive impairment, autism and epileptic encephalopathy with mild cerebellar symptoms. Eur J Hum Genet 23, 1505-1512 (2015).
L. F. Kuderna et al., A global catalog of whole-genome diversity from 233 primate species. bioRxiv 2023.05.02.538995 [Preprint] (2023).
L. M. Starita et al., Massively Parallel Functional Analysis of BRCA1 RING Domain Variants. Genetics 200, 413-422 (2015).
L. S. Johnson, S. R. Eddy, E. Portugaly, Hidden Markov model speed heuristic and iterative HMM search procedure. BMC Bioinformatics11, 431 (2010).
L. Sundaram et al., Predicting the clinical impact of human mutation with deep neural networks. Nat Genet 50, 1161-1170 (2018).
L. Wang et al., A high-quality genome assembly for the endangered golden snub-nosed monkey (*Rhinopithecus roxellana*). Gigascience 8, (2019).
L. Yu et al., Genomic analysis of snub-nosed monkeys (*Rhinopithecus*) identifies genes and processes related to high-altitude adaptation. Nat Genet 48, 947-952 (2016).

(56) References Cited

OTHER PUBLICATIONS

L. Zhang et al., SLCO1B1: Application and Limitations of Deep Mutational Scanning for Genomic Missense Variant Function. Drug Metab Dispos, DMD-AR-2020-000264 (2021).
M. A. Chiasson et al., Multiplexed measurement of variant abundance and activity reveals VKOR topology, active site and human variant impact. eLife 9, (2020).
M. A. Eberle et al., A reference data set of 5.4 million phased human variants validated by genetic inheritance from sequencing a three-generation 17-member pedigree. Genome Res 27, 157-164 (2017).
M. Baek et al., Accurate prediction of protein structures and interactions using a three-track neural network. Science373, 871-876 (2021).
M. de Manuel et al., Chimpanzee genomic diversity reveals ancient admixture with bonobos. Science 354, 477-481 (2016).
M. Ekeberg, C. Lövkvist, Y. Lan, M. Weigt, E. Aurell, Improved contact prediction in proteins: Using pseudolikelihoods to infer Potts models. Physical Review E 87, 012707 (2013).
M. H. Chaleshtori et al., High carrier frequency of the GJB2 mutation (35delG) in the north of Iran. International journal of pediatric otorhinolaryngology 71, 863-867 (2007).
M. J. Landrum et al., ClinVar: public archive of interpretations of clinically relevant variants. Nucleic Acids Res 44, D862-868 (2016).
M. Kallberg et al., Template-based protein structure modeling using the RaptorX web server. Nat Protoc 7, 1511-1522 (2012).
M. Lek et al., Analysis of protein-coding genetic variation in 60,706 humans. Nature 536, 285-291 (2016).
M. M. Awad et al., Acquired Resistance to KRASG12C Inhibition in Cancer. New England Journal of Medicine 384, 2382-2393 (2021).
M. Mirdita et al., Uniclust databases of clustered and deeply annotated protein sequences and alignments. Nucleic Acids Research 45, D170-D176 (2017).
M. Seuma, A. J. Faure, M. Badia, B. Lehner, B. Bolognesi, The genetic landscape for amyloid beta fibril nucleation accurately discriminates familial Alzheimer's disease mutations. eLife 10, e63364 (2021).
M. Slatkin, A population-genetic test of founder effects and implications for Ashkenazi Jewish diseases. The American Journal of Human Genetics 75, 282-293 (2004).
M. Stef et al., Spectrum of CREBBP gene dosage anomalies in Rubinstein-Taybi syndrome patients. Eur J Hum Genet 15, 843-847 (2007).
M. Steinegger et al., HH-suite3 for fast remote homology detection and deep protein annotation. BMC Bioinformatics 20, 473 (2019).
M. Varadi et al., AlphaFold Protein Structure Database: massively expanding the structural coverage of protein-sequence space with high-accuracy models. Nucleic Acids Research, (2021).
N. M. Ioannidis et al., REVEL: An Ensemble Method for Predicting the Pathogenicity of Rare Missense Variants. Am J Hum Genet 99, 877-885 (2016).
N. Malhis, M. Jacobson, S. J. M. Jones, J. Gsponer, LIST-S2: taxonomy based sorting of deleterious missense mutations across species. Nucleic Acids Research 48, W154-W161 (2020).
N. Osada, K. Matsudaira, Y. Hamada, S. Malaivijitnond, Testing sex-biased admixture origin of macaque species using autosomal and X-chromosomal genomic sequences. Genome Biol. Evol. 13, (2021).
N. Shah et al., Identification of Misclassified ClinVar Variants via Disease Population Prevalence. Am J Hum Genet 102, 609-619 (2018).
N. Srivastava, G. Hinton, A. Krizhevsky, I. Sutskever, R. Salakhutdinov, Dropout: A Simple Way to Prevent Neural Networks from Overfitting. Journal of Machine Learning Research 15, 1929-1958 (2014).
N. Whiffin et al., using high-resolution variant frequencies to empower clinical genome interpretation. Genet Med 19, 1151-1158 (2017).
N.-L. Sim et al., SIFT web server: predicting effects of amino acid substitutions on proteins. Nucleic Acids Research 40, W452-457 (2012).
O. Campuzano et al., Reanalysis and reclassification of rare genetic variants associated with inherited arrhythmogenic syndromes. EBioMedicine 54, 102732 (2020).
P. Bandaru et al., Deconstruction of the Ras switching cycle through saturation mutagenesis. Elife 6, (2017).
P. D. Stenson et al., The Human Gene Mutation Database: building a comprehensive mutation repository for clinical and molecular genetics, diagnostic testing and personalized genomic medicine. Hum Genet 133, 1-9 (2014).
P. D. Stenson, E. Ball, K. Howells, A. Phillips, M. Mort, D. N. Cooper, Human Gene Mutation Database: Towards a comprehensive central mutation database. J. Med. Genet.45, 124-126 (2008).
P. D. Stenson, M. Mort, E. V. Ball, M. Chapman, K. Evans, L. Azevedo, M. Hayden, S. Heywood, D. S. Millar, A. D. Phillips, D. N. Cooper, The Human Gene Mutation Database (HGMD®): Optimizing its use in a clinical diagnostic or research setting. Hum. Genet.139, 1197-1207 (2020).
P. D'Adamo et al., Does epidermal thickening explain GJB2 high carrier frequency and heterozygote advantage? European Journal of Human Genetics 17, 284-286 (2009).
P. Fiziev, e. al., Rare penetrant mutations confer severe risk of common diseases; Science; Jun. 2, 2023; vol. 380, Issue 6648; DOI: 10.1126/science.abo1131.
P. J. Cock et al., Biopython: freely available Python tools for computational molecular biology and bioinformatics. Bioinformatics 25, 1422-1423 (2009).
P. K. Albers, G. McVean, Dating genomic variants and shared ancestry in population-scale sequencing data. PLoS biology 18, e3000586 (2020).
P. Micikevicius et al., Mixed Precision Training. International Conference on Learning Representations, (2018).
P. Rentzsch, M. Schubach, J. Shendure, M. Kircher, CADD-Splice-improving genome-wide variant effect prediction using deep learning-derived splice scores. Genome Medicine 13, 31 (2021).
R. Do et al., No evidence that selection has been less effective at removing deleterious mutations in Europeans than in Africans. Nature Genetics 47, 126-131 (2015).
R. K. Pasumarthi et al., TF-Ranking: Scalable TensorFlow Library for Learning-to-Rank. Proceedings of the 25th ACM SIGKDD International Conference on Knowledge Discovery and Data Mining, 2970-2978 (2019).
R. K. Rowntree, A. Harris, The phenotypic consequences of CFTR mutations. Annals of human genetics 67, 471-485 (2003).
R. L. Nussbaum, H. L. Rehm, ClinGen, ClinGen and Genetic Testing. N Engl J Med 373, 1379 (2015).
R. M. Rao, J. Liu, R. Verkuil, J. Meier, J. Canny, P. Abbeel, T. Sercu, A. Rives, MSA Transformer in Proceedings of the 38th International Conference on Machine Learning, pp. 8844-8856 (2021).
R. N. Gutenkunst, R. D. Hernandez, S. H. Williamson, C. D. Bustamante, Inferring the joint demographic history of multiple populations from multidimensional SNP frequency data. PLoS Genet 5, e1000695 (2009).
R. Steinhaus et al., MutationTaster2021. Nucleic Acids Research 49, W446-W451 (2021).
R. W. Newberry, J. T. Leong, E. D. Chow, M. Kampmann, W. F. DeGrado, Deep mutational scanning reveals the structural basis for α-synuclein activity. Nature Chemical Biology 16, 653-659 (2020).
S. A. Sawyer, D. L. Hartl, Population genetics of polymorphism and divergence. Genetics 132, 1161-1176 (1992).
S. A. Schroeder, D. M. Gaughan, M. Swift, Protection against bronchial asthma by CFTR delta F508 mutation: a heterozygote advantage in cystic fibrosis. Nature medicine 1, 703-705 (1995).
S. A. Wilcox et al., High frequency hearing loss correlated with mutations in the GJB2 gene. Human genetics 106, 399-405 (2000).
S. C. Jin et al., Contribution of rare inherited and de novo variants in 2,871 congenital heart disease probands. Nat Genet 49, 1593-1601 (2017).
S. Caspar et al., Clinical sequencing: from raw data to diagnosis with lifetime value. Clinical genetics 93, 508-519 (2018).
S. De Rubeis et al., Synaptic, transcriptional and chromatin genes disrupted in autism. Nature 515, 209-215 (2014).

(56) References Cited

OTHER PUBLICATIONS

S. E. Bojesen et al., Multiple independent variants at the TERT locus are associated with telomere length and risks of breast and ovarian cancer. Nature genetics 45, 371-384 (2013).
S. F. Altschul, W. Gish, W. Miller, E. W. Myers, D. J. Lipman, Basic local alignment search tool. J Mol Biol 215, 403-410 (1990).
S. Gudmundsson et al., Genome Aggregation Database Consortium, Addendum: The mutational constraint spectrum quantified from variation in 141,456 humans. Nature 597, E3-E4 (2021).
S. J. Sanders et al., De novo mutations revealed by whole-exome sequencing are strongly associated with autism. Nature 485, 237-241 (2012).
S. J. Sanders et al., Insights into Autism Spectrum Disorder Genomic Architecture and Biology from 71 Risk Loci. Neuron 87, 1215-1233 (2015).
S. Rajbhandari, J. Rasley, O. Ruwase, Y. He, "ZeRO: Memory Optimizations Toward Training Trillion Parameter Models" in Proceedings of the International Conference for High Performance Computing, Networking, Storage and Analysis. (IEEE Press, 2020), pp. 1-16.
S. Richards et al., Standards and guidelines for the interpretation of sequence variants: a joint consensus recommendation of the American College of Medical Genetics and Genomics and the Association for Molecular Pathology. Genet Med 17, 405-424 (2015).
S. Wang, W. Li, S. Liu, J. Xu, RaptorX-Property: a web server for protein structure property prediction. Nucleic Acids Res 44, W430-435 (2016).
Schubert Benjamin et al: "Genome-wide discovery of epistatic loci affecting antibiotic resistance in Neisseria gonorrhoeae using evolutionary couplings", Nature Microbiology, Nature Publishing Group UK, London, vol. 4, No. 2, Dec. 3, 2018 (Dec. 3, 2018), pp. 328-338, XP036679933, DOI: 10.1038/S41564-018-0309-1.
Shan Gao et al: "Prediction of function changes associated with single-point protein mutations using support vector machines (SVMs)", Human Mutation, John Wiley & Sons, Inc, US, vol. 30, No. 8, May 20, 2009 (May 20, 2009), pp. 1161-1166,.
Smith Benjamin et al: "Sequence Imputation of HPV16 Genomes for Genetic Association Studies", PLOS ONE, [Online] vol. 6, No. 6, Jun. 23, 2011 (Jun. 23, 2011), p. e21375, XP093039157, DOI: 10.1371/journal.pone.0021375 Retrieved from the Internet: URL: https://journals.plos.org/plosone/article/file?id=10.1371/journal.pone.0021375&type=printable> [retrieved on Apr. 21, 2023].
T. J. Aitman et al., Malaria susceptibility and CD36 mutation. Nature 405, 1015-1016 (2000).
T. L. Mighell, S. Evans-Dutson, B. J. O'Roak, A Saturation Mutagenesis Approach to Understanding PTEN Lipid Phosphatase Activity and Genotype-Phenotype Relationships. American journal of human genetics 102, 943-955 (2018).
T. Ohta, Slightly deleterious mutant substitutions in evolution. Nature 246, 96-98 (1973).
V. E. Gray et al., Elucidating the Molecular Determinants of Aβ Aggregation with Deep Mutational Scanning. G3 (Bethesda) 9, 3683-3689 (2019).
W. Fu et al., Analysis of 6,515 exomes reveals the recent origin of most human protein-coding variants. Nature 493, 216-220 (2013).
W. J. Kent, C. W. Sugnet, T. S. Furey, K. M. Roskin, T. H. Pringle, A.M. Zahler, D. Haussler, The human genome browser at UCSC. Genome Res. 12, 996-1006 (2002).
Wu Martin et al: "Accounting for Alignment Uncertainty in Phylogenomics", PLOS ONE, vol. 7, No. 1, Jan. 17, 2012, p. e30288, XP093044217, DOI: 10.1371/journal.pone.0030288.
X. Huang et al., Inferring genome-wide correlations of mutation fitness effects between populations. Molecular Biology and Evolution.
X. Jia et al., Massively parallel functional testing of MSH2 missense variants conferring Lynch syndrome risk. American journal of human genetics 108, 163-175 (2021).
X. Liu, C. Li, C. Mou, Y. Dong, Y. Tu, dbNSFP v4: a comprehensive database of transcript-specific functional predictions and annotations for human nonsynonymous and splice-site SNVs. Genome Medicine 12, 103 (2020).
X. Liu, C. Wu, C. Li, E. Boerwinkle, dbNSFP v3.0: A One-Stop Database of Functional Predictions and Annotations for Human Nonsynonymous and Splice-Site SNVs. Hum Mutat 37, 235-241 (2016).
Y. B. Simons, M. C. Turchin, J. K. Pritchard, G. Sella, The deleterious mutation load is insensitive to recent population history. Nature genetics 46, 220-224 (2014).
Y. Benjamini, Y. Hochberg, Controlling the False Discovery Rate: A Practical and Powerful Approach to Multiple Testing. J. R. Stat. Soc. B57, 289-300 (1995).
Y. Choi, G. E. Sims, S. Murphy, J. R. Miller, A. P. Chan, Predicting the functional effect of amino acid substitutions and indels. PLoS One 7, e46688 (2012).
Y. E. Kim, C. S. Ki, M. A. Jang, Challenges and Considerations in Sequence Variant Interpretation for Mendelian Disorders. Ann Lab Med 39, 421-429 (2019).
Y. Yang et al., Molecular findings among patients referred for clinical whole-exome sequencing. Jama 312, 1870-1879 (2014).
Y. You et al., Pseudo-Lidar++: Accurate Depth for 3D Object Detection in Autonomous Driving; in International Conference on Learning Representations. (2020).
Y. You et al., Large Batch Optimization for Deep Learning: Training BERT in 76 Minutes; in International Conference on Learning Representations. (2020).
Y. Zhang, J. Skolnick, Scoring function for automated assessment of protein structure template quality. Proteins57, 702-710 (2004).
Z. Fan et al., Ancient hybridization and admixture in macaques (genus *Macaca*) inferred from whole genome sequences. Mol Phylogenet Evol 127, 376-386 (2018).
Z. Liu et al., Genomic Mechanisms of Physiological and Morphological Adaptations of Limestone Langurs to Karst Habitats. Mol Biol Evol 37, 952-968 (2020).
Balanya Sergio A et al., "Adaptive temperature scaling for Robust calibration of deep neural networks", Neural Computing and Applications, vol. 36, No. 14, Jul. 31, 2022 (Jul. 31, 2022), pp. 8073-8095, XP093174474, London ISSN: 0941-0643, DOI: 10.1007/s00521-024-09505-4.
B. Li, D. M. Roden, and J. A. Capra, "The 3D Mutational Constraint on Amino Acid Sites in the Human Proteome", Nature Communications, vol. 13, No. 1, p. 3273, 15 pages, Jun. 2022, doi: 10.1038/s41467-022-30936-x.
Chang Li, Degui hi, Kai Wang and Xiaoming Liu "MetaRNN: Differentiating Rare Pathogenic and Rare Benign Missense SNVs and InDels using Deep Learning", Genome Medicine, 14:115, pp. 1-14, Oct. 8, 2022, https://doi.org/10.1186/s13073-022-01120-z.
Chuan Guo et al., "On Calibration of Modern Neural Networks," ICML, 1231-1330 (2017). https://arxiv.org/pdf/1706.04599v2.pdf.
Dimitrios Vitsios et al., "Prioritizing non-coding regions based on human genomic constraint and sequence context with deep learning", Nature Communications 12, 1504, 14 pages, (2021). https://www.nature.com/articles/s41467-021-21790-4.
Felipe Antonio De Oliveria Garcis, "Insights on variant analysis in silico tools for pathogenicity prediction", Frontiers in Genetics, vol. 13, 14 pages, Nov. 29, 2022 (Nov. 29, 2022), XP093157045, Switzerland ISSN: 1664-8021, DOI: 10.3389/fgene.2022.1010327 Retrieved from the Internet: URL: https://www.ncbi.nlm.nih.gov/pmc/articles/PMC9774026/pdf/fgene-13-1010327.pdf>.
H-C. Chen, J. Wang, Q. Liu, and Y. Shyr, "A Domain Damage Index to Prioritizing the Pathogenicity of Missense Variants", (Author Manuscript) In PCM PubMed Central, 28 pages, Nov. 1, 2022, https://pmc.ncbi.nlm.nih.gov/articles/PMC8511099/.
H. Gao et al. "Supplementary Materials for The Landscape of Tolerated Genetic Variation in Human and Primates", Science 380, eabn8197, 88 pages, (2023) DOI: 10.1126/science.abn8197.
Hongjian Qi, Haicang Zhang, Yige Zhao, Chen Chen, John J Long, Wendy K. Chung et al. "MVP Predicts the Pathogenicity of Missense Variants by Deep Learning", Nature Communications, 12, 510, 9 pages, Jan. 21, 2021, https://doi.org/10.1038/s41467-020-20847-0.

(56) References Cited

OTHER PUBLICATIONS

I. Barrio-Hernandez et al., Network Expansion of Genetic Associations Defines a Pleiotropy Map of Human Cell Biology, Nature Genetics, vol. 55, No. 3, Art. No. 3, pp. 389-398, Mar. 2023, doi: 10.1038/s41588-023-01327-9.

Illumina "Protein Detection by Sequencing Towards a Definitive Cellular Phenotype", Natureresearch Custom Media, 5 pages, (2020) https://www.illumina.com/content/dam/illumina-marketing/documents/publications/nature_advertorial_Illumina_cite_seq.pdf.

John Jumper et al., "DeepMind—AlphaFold 2", DeepMind Technologies Limited, London, UK, 42 pages (2020). https://predictioncenter.org/casp14/doc/presentations/2020_12_01_TS_predictor_AlphaFold2.pdf.

J.M. Havrilla, B. S. Pedersen, R. M. Layer, and A. R. Quinlan, "A Map of Constrained Coding Regions in the Human Genome", In PCM PubMed Central (Author Manuscript), 25 pages, Jul. 1, 2019, https://pmc.ncbi.nlm.nih.gov/articles/PMC6589356/.

J. Traynelis et al., "Optimizing Genomic Medicine in Epilepsy Through a Gene-Customized Approach to Missense Variant Interpretation", Genome Research vol. 27: 1715-1729 (Sept. 1, 2017), doi: 10.1101/gr.226589.117 or https://genome.cshlp.org/content/27/10/1715.full.pdf.

Jiaying Lai et al., "LYRUS: A Machine Learning Model for Predicting the Pathogenicity of Missense Variants," Bioinformatics Advances vol. 2, issue 1, pp. 1-10, (2021) https://pubmed.ncbi.nlm.nih.gov/35036922/.

Jun-ichi Takeda et al., "InMeRF: Prediction of Pathogenicity of Missense Variants by Individual Modeling for Each Amino Acid Substitution," NAR Genomics and Bioinformatics, vol. 2, No. 2, 11 pages, May 2020, https://pubmed.ncbi.nlm.nih.gov/33543123/.

Justas Dauparas & Fabian Fuchs, "AlphaFold 2 & Equivariance" 16 pages, (Dec. 17, 2020). https://fabianfuchsml.github.io/alphafold2/ [retrieved from the internet May 15, 2024].

K. Bai et al., "Pathogenicity Classification of Missense Mutations Based on Deep Generative Model", Computers in Biology and Medicine, vol. 170, 9 pages, (2024).

K. E. Samocha et al., "Regional Missense Constraint Improves Variant Deleteriousness Prediction", Jun. 12, 2017, 32 pages, bioRxiv. doi: 10.1101/148353.

Max-Heinrich Laves et al., "Well-calibrated Model Uncertainty with Temperature Scaling for Dropout Variational Inference," 4th Workshop on Bayesian Deep Learning, 8 pages (2019). https://arxiv.org/pdf/1909.13550v3.pdf.

"Pagerank—NetworkX 3.6.1 documentation", 3 pages, Accessed: Jan. 20, 2026. [Online]. Available: https://networkx.org/documentation/stable/reference/algorithms/generated/networkx.algorithms.link_analysis.pagerank_alg.pagerank.html.

Pranay Dugar, "Attention—Seq2Seq Models", Towards Data Science, 18 pages, (2019). https://towardsdatascience.com/day-1-2-attention-seq2seq-models-65df3f49e263.

Raul Gomez "Understanding Ranking Loss, Constrastive Loss, Margin Loss, Triplet Loss, Hinge Loss and all those confusing names", 20 pages, (2019). https://gombru.github.io/2019/04/03/ranking_loss/.

Rob Finn et al., "Ensemble Variation—Calculated Variant Consequences." Ensembl, 5 pages, 2025. <URL: https://useast.ensembl.org/info/genome/variation/prediction/predicted_data.html#:~:text=For%20each%20variant%20that%20is,may%20have%20on%20each%20transcript>.

Rob Finn et al., "Ensemble Variation—Pathogenicity Predictions." Ensembl, 6 pages, 2024. <URL: https://useast.ensembl.org/info/genome/variation/prediction/protein_function.html>.

S. Chen et al., "A Genome-Wide Mutational Constraint Map Quantified From Variation in 76,156 Human Genomes", bioRxiv, 42 pages, Jan. 2022, doi: 10.1101/2022.03.20.485034.

S. Petrovski, Q. Wang, E. L. Heinzen, A. S. Allen, and D. B. Goldstein, "Genic Intolerance to Functional Variation and the Interpretation of Personal Genomes", PLOS Genetic, vol. 9, No. 8, p. e1003709, 13 pages, Aug. 2013, doi: 10.1371/journal.pgen.1003709.

Shi-Yuan Tong, Ke Fan, Zai-Wei Zhou, Lin-Yun Liu, Shu-Qing Zhang et al. "mvPPT: A Highly Efficient and Sensitive Pathogenicity Prediction Tool for Missense Variants", Genomics Proteomics Bioinformatics 21: pp. 414-426, Aug. 5, 2022, https://doi:10.1016/j.gpb.2022.07.005.

Thomas Willems et al., "Genome-wide profiling of heritable and de novo STR variations", Nat Methods (Author Manuscript), 14(6), 15 pages, (2017), https://www.ncbi.nlm.nih.gov/pmc/articles/PMC5482724/pdf/nihms864151.pdf.

Tiernan Ray, "DeepMind's AlphaFold 2 reveal: Convolutions are out, attention is in", ZDNET, 21 pages, (Jul. 19, 2021). https://www.zdnet.com/article/deepminds-alphafold-2-reveal-what-we-learned-and-didnt-learn/ [retrieved from the internet May 15, 2024].

Travers Ching et al., "Opportunities and obstacles for deep learning in biology and medicine", Journal of the Royal Society Interface, The Royal Society, London, GB, vol. 15, No. 20170387, Apr. 4, 2018 (Apr. 4, 2018), pp. 1-47, XP002789257, ISSN: 1742-5689, DOI: 10.1098/RSIF.2017.0387.

V. Seplyarskiy et al., "A Mutation Rate Model at the Basepair Resolution Identifies the Mutagenic Effect of Polymerase III Transcription", (Author Manuscript), In PCM PubMed Central, 28 pages, Aug. 27, 2024, https://pmc.ncbi.nlm.nih.gov/articles/PMC11348951/.

W. Lin et al., "Enhancing Missense Variant Pathogenicity Prediction with Protein Language Models Using VariPred", Scientific Reports, 14:8136, 13 pages, 2024.

Wikipedia, The Free Encyclopedia. "Mann—Whitney U Test" Website: <https://en.wikipedia.org/wiki/Mann%E2%80%93Whitney_U_test>. 15 pages. [retrieved from the internet May 15, 2024].

Wikipedia, The Free Encyclopedia. "Position weight matrix" Website: <https://en.wikipedia.org/wiki/Position_weight_matrix>. 5 pages. [retrieved from the internet May 15, 2024].

Wikipedia, The Free Encyclopedia. "Transformer (deep learning architecture)" Website: <https://en.wikipedia.org/wiki/Transformer_(deep_learning_architecture)>. 20 pages. [retrieved from the internet May 15, 2024].

Wikipedia, The Free Encyclopedia. "Wilcoxon signed-rank test" Website: <https://en.wikipedia.org/wiki/Wilcoxon_signed-rank_test>. 15 pages. [retrieved from the internet May 15, 2024].

Wilcox Emma H et al., "Evaluating the 1-42 impact of in silica predictors on clinical variant classification", Genetics in Medicine, vol. 24, No. 4, Apr. 1, 2022 (Apr. 1, 2022), pp. 924-930, XP093174481, DOI: 10.1016/j.gim.2021.11.018.

Won Dhong-Gun et al., "3Cnet: pathogenicity prediction of human variants using multitask learning with evolutionary constraints", Bioinformatics, vol. 37, No. 24, Dec. 11, 2021 (Dec. 11, 2021), pp. 4626-4634, XP093039946, GB ISSN: 1367-4803, DOI: 10.1093/bioinformatics/btab529 Retrieved from the Internet: URL: https://academic.oup.com/bioinformatics/article-pdf/37/24/4626/41726674/btab529.pdf>.

Y. Wu et al., Improved Pathogenicity Prediction for Rate Human Missense Variants, In The American Journal of Human Genetics 108, pp. 1891-1906, 2021.

J. L. Ba, J. R. Kiros, G. E. Hinton, "Layer Normalization", In Advances in NIPS Deep Learning Symposium, Barcelona, Spain, Dec. 8, 2016, 14 pages, arXiv preprint arXiv:1607.06450v1.

Rendón, Javier Macho et al: "HPIPred: Host-pathogen interactome prediction with phenotypic scoring", Computational and Structural Biotechnology Journal, vol. 20, Nov. 21, 2022 (Nov. 21, 2022), pp. 6534-6542, XP093387484, Sweden ISSN: 2001-0370, DOI:10.1016/j.csbj.2022.11.026.

A. B. Zhang et al. "Inferring species membership using DNA sequences with back- propagation neural networks." Systematic Biology 57.2 (2008): 202-215 (Year: 2008).

A.R. Boyko, Williamson SH, Indap AR, Degenhardt JD, Hernandez RD, et al. (2008) Assessing the Evolutionary Impact of Amino Acid Mutations in the Human Genome. PLOS Genetics 4(5): e1000083 (Year: 2008).

Alexander Rives et al., Biological structure and function emerge from scaling unsupervised learning to 250 million protein sequences, Proceedings of the National Academy of Sciences, Apr. 5, 2021, 118(15), 1-12 (Year: 2021).

(56) References Cited

OTHER PUBLICATIONS

Alex Wells, Heckerman D, Torkamani A, Yin L, Sebat J, Ren B, Telenti A, di Iulio J. Ranking of non-coding pathogenic variants and putative essential regions of the human genome. Nat Commun. Nov. 20, 2019; 10(1):5241. doi: 10.1038/s41467-019-13212-3. PMID:31748530; PMCID: PMC6868241. (Year: 2019).
Antonio Rausell, Mohammadi P, McLaren PJ, Bartha I, Xenarios I, Fellay J, Telenti A. Analysis of stop-gain and frameshift variants in human innate immunity genes. PLoS Comput Biol. Jul. 24, 2014;10(7):e1003757. doi: 10.1371/journal.pcbi. 1003757. PMID:25058640; PMCID: PMC4110073. (Year: 2014).
Davo, Position weight matrix, Dave Tang's blog, Oct. 1, 2013, 1-8, https://davetang.org/muse/2013/10/01/position-weight-matrix/ (Year: 2013).
Evan H. Baugh, Simmons-Edler R, Muller CL, Alford RF, Volfovsky N, Lash AE, Bonneau R. Robust classification of protein variation using structural modelling and large-scale data integration. Nucleic Acids Res. Apr. 7, 2016;44(6):2501-13. doi: 10.1093/nar/gkw120. Epub Feb. 2, 20168. PMID: 26926108; PMCID: PMC482 (Year: 2016).
GeeksforGeeks. Group by Function in R using Dplyr, https://www.geeksforgeeks.org/r-language/group-by-function-in-r-using-dplyr/ (Year: 2021).
Jonathan A. Eisen, "Phylogenomics: improving functional predictions for uncharacterized genes by evolutionary analysis." Genome research 8.3 (1998): 163-167 (Year: 1998).
J. Thusberg, Ayodeji Olatubosun, and Mauno Vihinen. "Performance of mutation pathogenicity prediction methods on missense variants." Human mutation 32.4 (2011): 358-368. (Year: 2011).
Liu L, Sanderford MD, Patel R, Chandrashekar P, Gibson G, Kumar S. Biological relevance of computationally predicted pathogenicity of noncoding variants. Nat Commun. Jan. 18, 2019;10(1):330. doi: 10.1038/s41467-018-08270-y. PMID: 30659175;PMCID: PMC6338804. (Year: 2019).
M. A. Beaumont, Zhang W, Balding DJ. Approximate Bayesian computation in population genetics. Genetics. Dec. 2002; 162(4):2025-35. (Year: 2002).
Peter D Keightley, Lei Eary, Daniel L Halligan, Mark Kirkpatrick, Inference of Mutation Parameters and Selective Constraint in Mammalian Coding Sequences by Approximate Bayesian Computation, Genetics, vol. 187, Issue 4, Apr. 1, 2011, pp. 1153-1161, (Year: 2011).
P. Evans, et al. "Genetic variant pathogenicity prediction trained using disease-specific clinical sequencing data sets." Genome research 29.7 (2019): 1144-1151. (Year: 2019).
Thomas S. Rask et al. "Using expected sequence features to improve basecalling accuracy of amplicon pyrosequencing data." BMC Bioinformatics 17.1 (2016): 176 (Year: 2016).
Ruoqi Wei et al., Recent Advances in Variational Autoencoders with Representation Learning for Biomedical Informatics: A Survey, IEEE Access, Dec. 31, 2020, 9, 1-18 (Year: 2020).
(The Biostatistics Cookbook: The Most User Friendly Guide for the Bio/Medical Scientist. Wiley & Sons.) (Year: 2014).
V. Rajan. "A method of alignment masking for refining the phylogenetic signal of multiple sequence alignments." Molecular biology and evolution 30.3 (2013): 689-712. (Year: 2013).
Wenhao Gao et al., Deep Learning in Protein Structural Modeling and Design, Patterns, Cell Press Open Access, Dec. 11, 2020, 1 (9), 1-23 (Year: 2020).
Livesey, BJ, Marsh JA, Using deep mutational scanning to benchmark variant effect predictors and identify disease mutations. Mol Syst Biol. Jul. 2020;16(7):e9380. doi: 10.15252/msb.20199380. PMID: 32627955; PMCID: PMC7336272. (Year: 2020).

* cited by examiner

Multiple Sequence Alignment (MSA) 200

Uni-Weighted Summary Statistics 300

Residue Categories 150

Positions 114

| | | | | | | |
|---|---|---|---|---|---|---|
| A | 0 | 0 | 1/7 | 0 | 1/7 | 1/7 |
| R | 0 | 0 | 0 | 0 | 0 | 0 |
| N | 0 | 0 | 0 | 0 | 0 | 1/7 |
| D | 0 | 0 | 0 | 0 | 0 | 0 |
| C | 0 | 0 | 0 | 0 | 0 | 0 |
| Q | 0 | 0 | 0 | 0 | 0 | 2/7 |
| E | 0 | 1/7 | 0 | 0 | 0 | 2/7 |
| G | 0 | 0 | 0 | 0 | 3/7 | 0 |
| H | 0 | 0 | 0 | 0 | 0 | 1/7 |
| I | 0 | 0 | 1/7 | 1/7 | 0 | 0 |
| L | 1/7 | 0 | 2/7 | 3/7 | 0 | 0 |
| K | 0 | 4/7 | 0 | 0 | 1/7 | 0 |
| M | 0 | 0 | 0 | 0 | 0 | 0 |
| F | 5/7 | 0 | 1/7 | 0 | 0 | 0 |
| P | 0 | 2/7 | 0 | 1/7 | 0 | 0 |
| S | 0 | 0 | 0 | 0 | 2/7 | 0 |
| T | 0 | 0 | 0 | 0 | 0 | 0 |
| W | 0 | 0 | 0 | 0 | 0 | 0 |
| Y | 1/7 | 0 | 0 | 0 | 0 | 0 |
| V | 0 | 0 | 2/7 | 2/7 | 0 | 0 |
| - | 0 | 0 | 0 | 0 | 0 | 0 |

Sequence-to-Weight Mapping 320

| Sequence | Weight w |
|---|---|
| 1 | 1/7 |
| 2 | 1/7 |
| 3 | 1/7 |
| 4 | 1/7 |
| 5 | 1/7 |
| 6 | 1/7 |
| 7 | 1/7 |

Species Proximity-Agnostic Uniform Weighting Logic 330

$$f_i^A = \sum_s w[M_i^s = A]$$

Residue Category-Under-Analysis 230

$F_1^1$ $F_2^1$ $F_4^1$ $F_5^1$ $F_7^1$

Figure 3

Differentially-Weighted Summary Statistics 400

Residue Categories 150

Positions 114

| | | | | | | |
|---|---|---|---|---|---|---|
| A | 0 | 0 | 0.4/7 | 0 | 0.7/7 | 0.7/7 |
| R | 0 | 0 | 0 | 0 | 0 | 0 |
| N | 0 | 0 | 0 | 0 | 0 | 0.9/7 |
| D | 0 | 0 | 0 | 0 | 0 | 0 |
| C | 0 | 0 | 0 | 0 | 0 | 0 |
| Q | 0 | 0 | 0 | 0 | 0 | 0.9/7 |
| E | 0 | 0.8/7 | 0 | 0 | 0 | 1.4/7 |
| G | 0 | 0 | 0 | 0 | 1.8/7 | 0 |
| H | 0 | 0 | 0 | 0 | 0 | 0.3/7 |
| I | 0 | 0 | 0.5/7 | 0.8/7 | 0 | 0 |
| L | 0.8/7 | 0 | 1.2/7 | 1.9/7 | 0 | 0 |
| K | 0 | 2.3/7 | 0 | 0 | 0.6/7 | 0 |
| M | 0 | 0 | 0 | 0 | 0 | 0 |
| F | 2.9/7 | 0 | 0.8/7 | 0 | 0 | 0 |
| P | 0 | 1.1/7 | 0 | 0.4/7 | 0 | 0 |
| S | 0 | 0 | 0 | 0 | 1.1/7 | 0 |
| T | 0 | 0 | 0 | 0 | 0 | 0 |
| W | 0 | 0 | 0 | 0 | 0 | 0 |
| Y | 0.5/7 | 0 | 0 | 0 | 0 | 0 |
| V | 0 | 0 | 1.3/7 | 1.1/7 | 0 | 0 |
| - | 0 | 0 | 0 | 0 | 0 | 0 |

Sequence-to-Weight Mapping 420

| Sequence | Weight $w_s$ |
|---|---|
| 1 | 0.3/7 |
| 2 | 0.4/7 |
| 3 | 0.5/7 |
| 4 | 0.6/7 |
| 5 | 0.7/7 |
| 6 | 0.8/7 |
| 7 | 0.9/7 |

Species Proximity-Aware Differential Weighting Logic 430

$$f'^{A}_{i} = \sum_s w_s[M_i^s = A]$$

Residue Category-Under-Analysis 230

$F_1^1$ $F_2^1$ $F_4^1$ $F_5^1$ $F_7^1$

Figure 4

Generation of Weighted Evolutionary Profiles 500

Voxelized Depiction of Figure 9 1000

SPECIES PROXIMITY-AWARE EVOLUTIONARY CONSERVATION PROFILES

PRIORITY APPLICATIONS

This application claims priority to or the benefit the following applications:

U.S. Provisional Patent Application No. 63/294,830, titled "Species-differentiable Evolutionary Profiles," by Tobias H A M P and Kai-How F A R H, filed Dec. 29, 2021.

U.S. Provisional Patent Application No. 62/294,828, titled "Inter-Model Prediction Score Recalibration," by Tobias H A M P and Kai-How F A R H, filed Dec. 29, 2021;

U.S. Provisional Patent Application No. 63/294,827, titled "Deep Learning Network for Evolutionary Conservation," by Sabrina RASHID and Kai-How F A R H, filed Dec. 29, 2021;

U.S. Provisional Patent Application No. 63/294,820, titled "Identifying Genes With Differential Selective Constraint Between Humans And Non-human Primates," by Hong GAO, Joshua Goodwin Jon MCMASTER-SCHRAIBER, Kai-How F A R H, filed Dec. 29, 2021;

U.S. Provisional Patent Application No. 63/294,816, titled "Classifying Millions of Variants of Uncertain Significance Using Primate Sequencing And Deep Learning," by Hong GAO, Tobias H A M P, Joshua Goodwin Jon MCMASTER-SCHRAIBER, Laksshman SUNDARAM, Kai-How F A R H, filed Dec. 29, 2021; and U.S. Provisional Patent Application No. 63/294,813, titled "Periodic Mask Pattern for Revelation Language Models," by Tobias H A M P, Anastasia Susanna Dagmar DIETRICH, Yibing W U, Jeffrey Mark E D E, Kai-How F A R H, filed Dec. 29, 2021;

The priority provisional applications are hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using neural networks to analyze ordered data.

INCORPORATIONS

The following are incorporated by reference for all purposes as if fully set forth herein:

Sundaram, L. et al. Predicting the clinical impact of human mutation with deep neural networks. *Nat. Genet.* 50, 1161-1170 (2018) (hereinafter "PrimateAI");

Jaganathan, K. et al. Predicting splicing from primary sequence with deep learning. Cell 176, 535-548 (2019) (hereinafter "SpliceNet");

U.S. Provisional Patent Application No. 62/573,144, titled "TRAINING A DEEP PATHOGENICITY CLASSIFIER USING LARGE-SCALE BENIGN TRAINING DATA," filed Oct. 16, 2017 (hereinafter "PrimateAI");

U.S. Provisional Patent Application No. 62/573,149, titled "PATHOGENICITY CLASSIFIER BASED ON DEEP CONVOLUTIONAL NEURAL NETWORKS (CNNs)," filed Oct. 16, 2017 (hereinafter "PrimateAI");

U.S. Provisional Patent Application No. 62/573,153, titled "DEEP SEMI-SUPERVISED LEARNING THAT GENERATES LARGE-SCALE PATHOGENIC TRAINING DATA," filed Oct. 16, 2017 (hereinafter "PrimateAI");

U.S. Provisional Patent Application No. 62/582,898, titled "PATHOGENICITY CLASSIFICATION OF GENOMIC DATA USING DEEP CONVOLUTIONAL NEURAL NETWORKS (CNNs)," filed Nov. 7, 2017 (hereinafter "PrimateAI");

U.S. Nonprovisional patent application Ser. No. 16/160,903, titled "DEEP LEARNING-BASED TECHNIQUES FOR TRAINING DEEP CONVOLUTIONAL NEURAL NETWORKS," filed on Oct. 15, 2018 (hereinafter "PrimateAI");

U.S. Nonprovisional patent application Ser. No. 16/160,986, titled "DEEP CONVOLUTIONAL NEURAL NETWORKS FOR VARIANT CLASSIFICATION," filed on Oct. 15, 2018 (hereinafter "PrimateAI");

U.S. Nonprovisional patent application Ser. No. 16/160,968, titled "SEMI-SUPERVISED LEARNING FOR TRAINING AN ENSEMBLE OF DEEP CONVOLUTIONAL NEURAL NETWORKS," filed on Oct. 15, 2018 (hereinafter "PrimateAI");

U.S. Nonprovisional patent application Ser. No. 16/407,149, titled "DEEP LEARNING-BASED TECHNIQUES FOR PRE-TRAINING DEEP CONVOLUTIONAL NEURAL NETWORKS," filed May 8, 2019 (hereinafter "PrimateAI");

U.S. Nonprovisional patent application Ser. No. 17/232,056, titled "DEEP CONVOLUTIONAL NEURAL NETWORKS TO PREDICT VARIANT PATHOGENICITY USING THREE-DIMENSIONAL (3D) PROTEIN STRUCTURES," filed on Apr. 15, 2021, (hereinafter "PrimateAI 3D");

U.S. Provisional Patent Application No. 63/175,495, titled "MULTI-CHANNEL PROTEIN VOXELIZATION TO PREDICT VARIANT PATHOGENICITY USING DEEP CONVOLUTIONAL NEURAL NETWORKS," filed on Apr. 15, 2021, (hereinafter "PrimateAI 3D");

U.S. Provisional Patent Application No. 63/175,767, titled "EFFICIENT VOXELIZATION FOR DEEP LEARNING," filed on Apr. 16, 2021, (hereinafter "PrimateAI 3D");

U.S. Nonprovisional patent application Ser. No. 17/468,411, titled "ARTIFICIAL INTELLIGENCE-BASED ANALYSIS OF PROTEIN THREE-DIMENSIONAL (3D) STRUCTURES," filed on Sep. 7, 2021, (hereinafter "PrimateAI 3D");

U.S. Provisional Patent Application No. 63/229,897, titled "TRANSFER LEARNING-BASED USE OF PROTEIN CONTACT MAPS FOR VARIANT PATHOGENICITY PREDICTION," filed on Aug. 5, 2021, (hereinafter "PrimateAI 2D");

U.S. Provisional Patent Application No. 63/253,122, titled "PROTEIN STRUCTURE-BASED PROTEIN LANGUAGE MODELS," filed Oct. 6, 2021 (hereinafter "JigsawAI");

U.S. Provisional Patent Application No. 63/281,579, titled "PREDICTING VARIANT PATHOGENICITY FROM EVOLUTIONARY CONSERVATION USING THREE-DIMENSIONAL (3D) PROTEIN STRUCTURE VOXELS," filed Nov. 19, 2021 (hereinafter "JigsawAI");

U.S. Provisional Patent Application No. 63/281,592, titled "COMBINED AND TRANSFER LEARNING OF A VARIANT PATHOGENICITY PREDICTOR USING GAPED AND NON-GAPED PROTEIN SAMPLES," filed Nov. 19, 2021 (hereinafter "JigsawAI");

U.S. Nonprovisional patent application Ser. No. 17/533,091, titled "PROTEIN STRUCTURE-BASED PROTEIN LANGUAGE MODELS," filed on Nov. 22, 2021, (hereinafter "JigsawAI");

U.S. Provisional Patent Application No. 63/304,544, titled "IMAGE-BASED VARIANT PATHOGENICITY DETERMINATION," filed Jan. 28, 2022; and U.S. Provisional Patent Application No. 63/304,308, titled "INDEL PATHOGENICITY DETERMINATION," filed Jan. 28, 2022.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Predicting functional consequences of variants relies at least in part on the assumption that crucial amino acids for protein families are conserved through evolution due to negative selection (i.e., amino acid changes at these sites were deleterious in the past), and that mutations at these sites have an increased likelihood of being pathogenic (causing disease) in humans. Homologous sequences of a target protein are collected and aligned in a multiple sequence alignment (MSA). A metric of conservation is computed based on weighted scores and/or frequencies of different amino acids observed in the target position in the MSA.

An MSA is generally the alignment of three or more biological sequences, protein, or nucleic acid, of similar length. From the alignment, the degree of homology can be inferred and the evolutionary relationships among the sequences studied. An MSA is also a tool used to identify the evolutionary relationships and common patterns among genes. Alignments are generated and analyzed using computational algorithms. Dynamic and heuristic approaches are used in most MSA algorithms. One of the objectives of alignment is to detect structural or functional identities and similarities between residues in protein sequences relative to other protein sequences.

Homolog information pertaining to aligned sequences in the MSA can be represented by two matrices (evolutionary conservation metrics): a position-specific scoring matrix (PSSM) and a position-specific frequency matrix (PSFM). PSSMs and PSFMs reflect the conservation of residues at specific positions of protein chains based on evolutionary information.

PSSMs and PSFMs are agnostic to the different degrees of evolutionary proximity between the species of non-query sequences in the MSA and the species of a query sequence in the MSA. That is, varied evolutionary distances between species of non-query sequences in the MSA, and the species of a query sequence in the MSA are not accounted for in the PSSMs and PSFMs. Variants from all species and sequences in the MSA contribute equally to the PSSMs and PSFMs. For example, a variant in chimp (closely related to human) increases the frequency of an amino acid by the same amount as the same variant in Zebrafish (distant to human). Such a deficiency in the evolutionary conservation state information can cause inaccurate phenotype prediction.

Therefore, an opportunity arises to make evolutionary conservation metrics like PSSMs and PSFMs aware of the relative evolutionary proximities of non-query species to a query species in an MSA. More complete evolutionary conservation state information and more accurate phenotype prediction may result.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIG. 3 illustrates one implementation of generating "uni-weighted" summary statistics based on assigning a common (or constant) weight to all the sequences in the MSA of FIG. 2.

FIG. 4 illustrates one implementation of generating the disclosed "differential-weighted" summary statistics based on assigning respective weights to the respective sequences in the MSA of FIG. 2.

DETAILED DESCRIPTION

Figure 1:
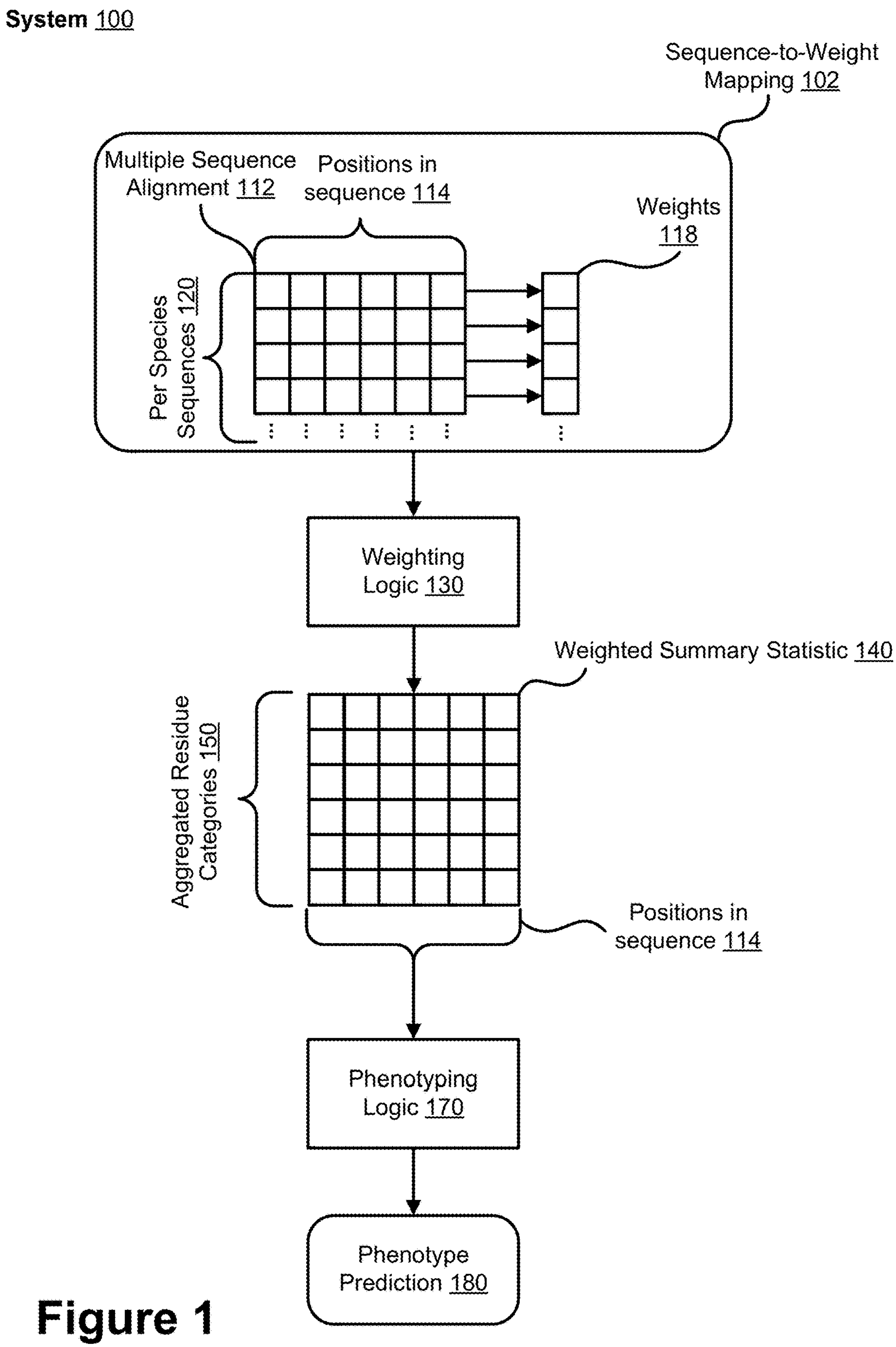
FIG. 1 depicts an example system that uses the disclosed weighting logic to generate a weighted summary statistic, which is in turn used for phenotype prediction in accordance with one implementation of the technology disclosed.

The following discussion is presented to enable any person skilled in the art to make and use the technology disclosed and is provided in the context of a particular application and its requirements. Various modifications to the disclosed implementations will be readily apparent to those skilled in the art, and the general principles defined herein can be applied to other implementations and applications without departing from the spirit and scope of the technology disclosed. Thus, the technology disclosed is not intended to be limited to the implementations shown but is to be accorded the widest scope consistent with the principles and features disclosed herein.

The detailed description of various implementations will be better understood when read in conjunction with the appended drawings. To the extent that the figures illustrate diagrams of the functional blocks of the various implementations, the functional blocks are not necessarily indicative of the division between hardware circuitry. Thus, for example, one or more of the functional blocks (e.g., modules, processors, or memories) can be implemented in a single piece of hardware (e.g., a general purpose signal processor or a block of random access memory, hard disk, or the like) or multiple pieces of hardware. Similarly, the programs can be stand-alone programs, can be incorporated as subroutines in an operating system, can be functions in an installed software package, and the like. It should be understood that the various implementations are not limited to the arrangements and instrumentality shown in the drawings.

The processing engines and databases of the figures, designated as modules, can be implemented in hardware or software, and need not be divided up in precisely the same blocks as shown in the figures. Some of the modules can also be implemented on different processors, computers, or servers, or spread among a number of different processors, computers, or servers. In addition, it will be appreciated that some of the modules can be combined, operated in parallel or in a different sequence than that shown in the figures without affecting the functions achieved. The modules in the figures can also be thought of as flowchart steps in a method. A module also need not necessarily have all its code disposed contiguously in memory; some parts of the code can be separated from other parts of the code with code from other modules or other functions disposed in between.

This discussion is organized as follows. First, we introduce the notion that existing evolutionary conservation profiles are agnostic to different degrees of evolutionary proximity between species. We then propose the technology disclosed as a solution to provide the missing differential evolutionary proximity context. This is followed by an example system that generates the disclosed weighted summary statistics and uses them for phenotype prediction. After that, we show an example multiple sequence alignment (MSA) and contrast calculating weighted summary statistics using a uni-weighted approach from the disclosed differentially-weighted approach. Advancing further, we give many examples of using the weighted summary statistics as inputs to a variety of deep neural networks for variant pathogenicity prediction and protein contact map generation. Finally, some particular implementations of the technology disclosed are discussed.

INTRODUCTION

Multiple sequence alignment (MSA) is an alignment of multiple homologous protein sequences to a target protein. MSA is an important step in comparative analyses and property prediction of biological sequences since a lot of information, for example, evolution and coevolution clusters, are generated from the MSA and can be mapped to a target sequence of choice or on the protein structure.

Sequence profiles of a protein sequence X of length L are an L×20 matrix, either in the form of a position-specific scoring matrix (PSSM) or a position-specific frequency matrix (PSFM), collectively position-specific matrices (PSMs). PSSMs represent the evolutionary conservation of alternate amino acids that are candidates for filling an amino acid vacancy in a vacancy-containing protein. PSSMs represent the evolutionary conservation of alternate amino acids based at least in part on structural (or spatial) compatibility between substitute amino acids and adjacent amino acids in a neighborhood of the amino acid vacancy (e.g., the right and left flanking amino acids around the amino acid vacancy). On the other hand, PSFMs represent the conservation of amino acids in a e.g., human protein sequence across aligned protein sequences of other species by determining, on a location-by-location basis, the frequency of occurrence of an amino acid in the human protein sequence across the aligned protein sequences of other species. PSFMs and PSSMs can be used to identify the evolutionary conservation profiles of homologous proteins of the plurality of species and differentiate most-conserved amino acids from non-conserved amino acids. In one implementation, the columns of a PSSM and a PSFM are indexed by the alphabet (or category) of amino acids, and each row corresponds to a position in the protein sequence X. PSSMs and PSFMs contain the substitution scores and the frequencies, respectively, of the amino acids at different positions in the protein sequence X. Each row of a PSFM is normalized to sum to one. The sequence profiles of the protein sequence X are computed by aligning X with multiple sequences in a protein database that have statistically significant sequence similarities with the protein sequence X. The sequence profiles contain more general evolutionary and structural information of the protein family that the protein sequence X belongs to, and thus, can be applied to various biological applications including phenotype prediction, evolutionary analysis, protein function prediction. One application of the sequence profiles of protein sequence X, for example, is to analyze the pathogenicity of variants when they are introduced in protein sequence X.

A protein sequence (called query sequence, e.g., a reference amino acid sequence of a protein) can be used as a seed to search and align homologous sequences from a protein database (e.g., SWISSPROT) using, for example, a PSI-BLAST program. The aligned sequences share some homologous segments and belong to the same protein family. The aligned sequences are further converted into two profiles to express their homologous information: PSSM and PSFM. Both PSSM and PSFM are matrices with twenty rows and L columns, where L is the total number of amino acids in the query sequence. Each column of a PSSM represents the log-likelihood of the residue substitutions at the corresponding positions in the query sequence. The (i, j)-th entry of the PSSM matrix represents the chance of the amino acid in the j-th position of the query sequence being mutated to amino acid type i during the evolution process. A PSFM contains the weighted observation frequencies of each position of the aligned sequences. Specifically, the (i, j)-th entry of the PSFM matrix represents the possibility of having amino acid type i in position j of the query sequence.

PSSMs and PSFMs are agnostic to the different degrees of evolutionary proximity between the species of non-query sequences in the MSA and the species of a query sequence in the MSA. That is, varied evolutionary distances between species of non-query sequences in the MSA, and the species of a query sequence in the MSA are not accounted for in the PSSMs and PSFMs. Variants from all species and sequences in the MSA contribute equally to the PSSMs and PSFMs. For example, a variant in chimp (closely related to human) increases the frequency of an amino acid by the same amount as the same variant in Zebrafish (distant to human). Such a deficiency in the evolutionary conservation state information can cause inaccurate phenotype prediction.

PSSMs and PSFMs, and their variants, are referred to herein as "evolutionary conservation metrics" or "evolutionary conservation measures" or "evolutionary profiles" or "evolutionary conservation summary statistics" or "conservation summary statistics" or "uni-weighted summary statistics," "summary statistics," or "PSMs."

The majority of available evolutionary conservation metrics use dynamically-generated profiles (e.g., using BLAST). As a result, the number of alignments and the set of species are different for each protein. Without constraining the number of species, it can reach into millions of species for a protein and make learning species weights impossible. The technology disclosed relies on the availability of whole-protein human sequence alignments. As an example, for only Multiz100 alignments (a group of multiple alignments of 100 vertebrate species and evolutionary conservation using phastCons and phyloP methods generated and made publicly available by the Genomics Institute at the University of California Santa Cruz), each species being weighted equally within the alignment is reasonable because the species included in Multiz100 were carefully selected and balanced by taxonomic ranks. However, the number of available whole proteome alignments is rapidly increasing, and as a result, redundancy and diversity between alignments also increase. Therefore, it is increasingly unclear how to optimally turn alignment data into high-quality evolutionary profiles. The technology disclosed provides a way to solve this problem automatically.

The technology disclosed generates evolutionary profiles like the PSSMs and PSFMs using weights assigned to per-species sequences in the MSA. The weights can be assigned proportional to the evolutionary proximity between a given species of a non-query sequence in the MSA and a target species of a query sequence in the MSA (or inversely proportional to the evolutionary distance between the given species and the target species). Greater weights can be assigned to those non-query sequences in the MSA whose species are evolutionary closer to the target species. Smaller weights are assigned to those non-query sequences in the MSA whose species are evolutionary farther from the target species. Proportional proximity can be a starting point, adjusted according to judgment of a researcher or a consensus among colleagues.

The assignment of weights can further be leveraged to determine the optimal alignment to use as input. A weighted evolutionary profile may be informative to a wide variety of genetics studies and thus, the input alignment that is optimal will be influenced by the target application for the evolutionary profile and can be expected to differ between distinct target applications. For example, certain applications of the disclosed system may benefit more from an input alignment comprising primarily evolutionarily proximate or primarily evolutionary distant species, while other applications may necessitate an evolutionary profile generated from a more diverse set of species.

The weights can be learned through backpropagation and may not be proportional to the evolutionary proximity among species. For example, training by backward propagation has revealed that presence of many sequencing or alignment errors can cause a lower weight to be learned for a species that is closely related to the target species than the weight for an accurately sequenced, well-aligned species at a greater evolutionary distance.

BLAST queries of a protein sequence database are not species-constrained. Thus, for each protein BLAST query, the number, type, and order of species returned in the MSA can vary. This makes it highly non-trivial to incorporate relationships among species in a machine learning model. For example, sequences corresponding to a plurality of species can be encoded and used to train a machine learning model. With millions of species, the weighting would have millions of per-species sequences; hence, also requiring millions of additional model parameters and millions of additional data samples to train the machine learning model. Alternatively, one can use phylogenic trees; however, this requires extra machine learning modules trained to deal with the structure and format of the phylogenic trees. Moreover, phylogenic trees can themselves contain errors and would abstract away precise species information. In contrast, the use of fixed-species MSAs (e.g., Multiz100 alignments) to calculate PSSMs and PSFMs improves interpretability of data because included species are consistent for each of the MSAs. Nevertheless, fixed-species MSAs may still face the challenge that every species, regardless of its evolutionary distance from human species, is treated in the same way.

The introduction of weighted PSSMs and weighted PSFMs addresses species homology and gene conservation (e.g., comparing monkeys to humans versus comparing fish to humans) and non-linear relationships between species with respect to human pathogenicity (e.g., the decision whether conservation of a certain amino acid in fish should be considered to predict human pathogenicity may depend on the presence of that amino acid in certain other primate species). Finally, the technology disclosed also addresses the valuable information that an entire protein region around a protein position in each species carries. For example, considering a window of ten amino acids rather than a single amino acid position may better reflect how similar a particular protein region from another species is to humans, and therefore the extent to which mutations in that region should be considered in the calculation of human pathogenicity in a mutation.

Scores and frequencies in the weighted PSSMs and weighted PSFMs generated by the technology disclosed are modulated by the weights assigned to the underlying sequences whose position-wise occurrences/hits (for example, of amino acids or nucleotides) contribute to the scores and frequencies. Greater weights assigned to sequences of evolutionary proximate species to the target species (where evolutionary proximate species refer to species with close evolutionary distance to the target species, as measured by the number of nucleotide substitutions per site between two homologous DNA sequences, or the number of amino acid substitutions per site between two homologous protein species, where evolutionary distance is inversely proportional to weight) can result in augmented/increased/enhanced scores and frequencies in the weighted PSSMs and weighted PSFMs generated by the technology disclosed. Smaller weights assigned to sequences of evolutionary distant species from the target species can result in attenuated/decreased/diminished scores and frequencies in the weighted PSSMs and weighted PSFMs generated by the technology disclosed. In other words, conservation information from closely related species (e.g., monkey) to human can be more informative with respect to phenotype prediction and pathogenicity prediction in human, compared to distantly related species (e.g., fish).

The technology disclosed also takes into consideration non-linear relationship among species-specific weights by using convolutions. Non-linear relationships exist among species with respect to human pathogenicity. For example, the decision whether conservation of an amino acid in fish should be considered to predict human pathogenicity may depend on the presence of that amino acid in a certain monkey species. The flexibility in the size of convolutional kernels allows capturing the context information of an amino acid or a protein site of interest. The phenotypic effect of a mutation at one genetic site often depends on alleles at other sites. As a result, any mutation is expected to be contingent on earlier mutations and the fate of this mutation depends on the evolutionary history thereof.

The technology disclosed can also use convolutional kernels with different sizes to process protein sites including the amino acid of interest as well as neighboring amino acids in the protein sites. For example, instead of only analyzing a single amino acid, a kernel size covering multiple amino acids in a protein site of interest can better reflect how similar this protein site from another species is to human and how far mutation should be considered in the calculation of pathogenicity of a mutation in human.

The disclosed weighted summary statistics are referred to herein as "weighted evolutionary conservation metrics" or "weighted evolutionary conservation measures" or "weighted evolutionary profiles" or "weighted evolutionary conservation summary statistics" or "weighted conservation summary statistics" or "differentially-weighted summary statistics" or "weighted summary statistics." Weighted position-specific scoring matrices (PSSMs) and weighted position-specific frequency matrices (PSFMs) are examples of the disclosed weighted summary statistics.

Implementations of the technology disclosed use the term "residue" and "amino acid" interchangeably. A person skilled in the art will appreciate that the technology disclosed can be analogously applied to other genomic/biological/chemical units and/or accumulations and/or combinations thereof, such as nucleotides, atoms, peptides, and so on. Similarly, the genomic/biological/chemical units can originate from a variety of natural and synthetic resources, such as DNA, RNA, proteins, and so on.

A person skilled in the art will also appreciate that the technology disclosed can be analogously applied to any biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound (s) such as analogs or mimetics of the aforementioned species.

System

FIG. 1 depicts an example system 100 that can use the disclosed weighting logic 130 to generate a weighted summary statistic 140, which is in turn used for phenotype prediction 180 in accordance with one implementation of the technology disclosed.

A sequence-to-weight mapping 102 assigns respective weights 118 to respective sequences 120 in a multiple sequence alignment (MSA) 112. Multiple sequence alignment (MSA) is a method for grouping a series of related proteins. MSA 112 arranges proteins in a matrix whose rows are individual protein sequences and whose columns contain amino acids that either come from the same position in some ancestral sequence (homologous) or play a common structural or functional role.

The weighting logic 130 has access to the sequence-to-weight mapping 102. The weighting logic 130 is configured to determine a weighted summary statistic 140. The weighted summary statistic 140 can be considered a weighted evolutionary conservation summary statistic in which the evolutionary conservation scores or frequencies are differentially weighted according to weights assigned to underlying sequences by the sequence-to-weight mapping 102. Determination of weights is discussed below.

In one implementation, the weighted summary statistic 140 is determined for a given residue category from residue categories 150 (e.g., twenty-one amino acid categories (including stop or gap amino acid category)) at a given position from positions 114 in the multiple sequence alignment (MSA) 112. In such an implementation, the weighted summary statistic 140 is based on one or more weights in the respective weights 118 of one or more sequences in the respective sequences 120 that have a residue of the given residue category at the given position. In some implementations, weights are initially assigned to be equal for all sequences within the alignment, and each respective weight is differentiable and learned during model training for system 100.

In some implementations, a phenotyping logic 170 is configured to generate the phenotype prediction 180 for the given position based on the weighted summary statistic 140. In some implementations, the phenotyping logic 170 can be a variant pathogenicity prediction logic (e.g., PrimateAI, PrimateAI 2D, PrimateAI 3D, JigsawAI). In other implementations, the phenotyping logic 170 can be a protein contact map generation logic. In yet other implementations, the phenotyping logic 170 can be a protein functionality prediction logic.

Residue Category-Under-Analysis

Figure 2:
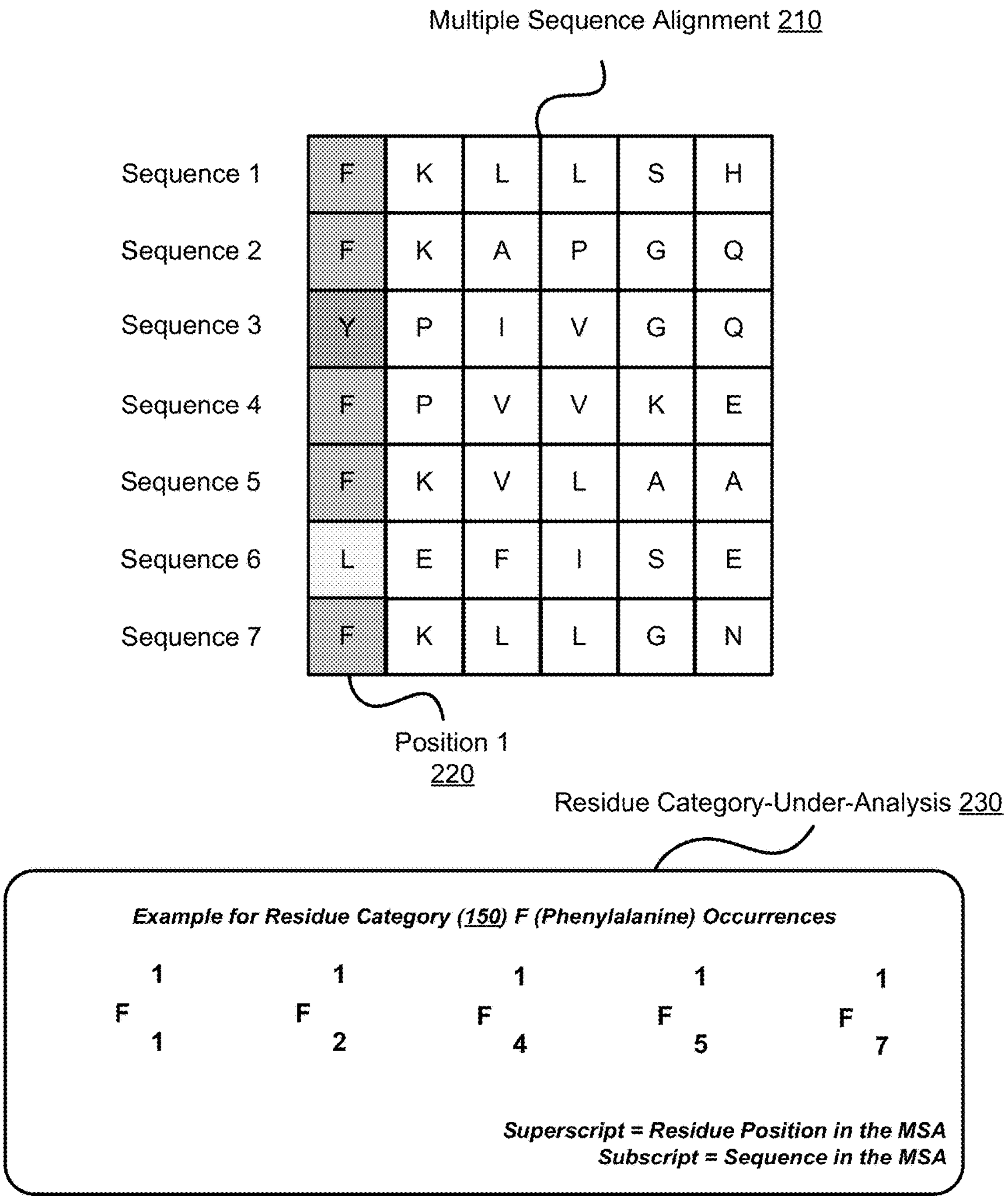
FIG. 2 shows an example of a multiple sequence alignment (MSA) and a residue category-under-analysis for which the disclosed weighted summary statistic is generated.

FIG. 2 shows an example of a multiple sequence alignment (MSA) 210 and a residue category-under-analysis 230 for which the disclosed weighted summary statistic is generated. N sequences in the MSA 210 can have the residue of the given residue category-under-analysis 230 at the given position 220. For example, in FIG. 2, five of the seven sequences in the MSA 210 have residue category F (Phenylalanine) at position1 220.

Uni-Weighted Summary Statistics

FIG. 3 illustrates one implementation of generating "uni-weighted" summary statistics 300 based on assigning a common weight (e.g., w=1) to all the sequences in the MSA 210 (i.e., using species proximity-agnostic uniform weighting logic 330).

The uni-weighted summary statistics 300 are a sum of N constant weights respectively assigned to the N sequences by a sequence-to-weight mapping 320. The sum is calculated using the species proximity-agnostic uniform weighting logic 330. Using amino acids in protein sequences as an example, let $\Sigma=\{A, \ldots, W, -\}$ be the set of all 20 amino acids A, . . . , W plus a gap token denoted as "-". M is an |S|-way multiple sequence alignment S (|S|=7 in this example) and $$M_i^s$$

is the amino acid at protein position i in sequence $s \in S$.

The evolutionary profile of an amino acid A at protein position i is defined as $$f_i^A = \sum_s w[M_i^s = A],$$

where [ ] is the Iverson bracket and $$w = \frac{1}{|S|}$$

is a normalization constant. Thus, all values are divided by 7 in this example. We interpret f as a signal for phenotype prediction. A constant w implies that variants from all species and sequences are equally important contributors and thus all have a weight of 1/7. For example, a variant in chimp (closely related to human) increases the frequency of an amino acid by the same amount as the same variant in Zebrafish (distant to human).

Differentially-Weighted Summary Statistics

FIG. 4 illustrates one implementation of generating the disclosed "differential-weighted" summary statistics 400 based on assigning respective weights to the respective sequences in the MSA 210 (i.e., using species proximity-aware differential weighting logic 430).

In the implementation illustrated in FIG. 4, each of the sequences 1-7 in the MSA 210 is assigned a different weight by a sequence-to-weight mapping 420. In some implementations, the weights are sequence-specific. In other implementations, the weights are species-specific (i.e., two or more sequences in the MSA 210 from a same species are assigned a same weight). In one implementation, some sequences and/or species in the MSA can share a weight while other sequences and/or species in the MSA can have different weights.

Next, a species proximity-aware differential weighting logic 430 is discussed. We disclose a new weighted evolutionary profile $$f'^A_i = \Sigma_S w_S[M_i^S = A],$$

where $w_s$ is the weight of each sequence. As shown in FIG. 4, i=1, S={$S_1$, $S_2$, $S_3$, $S_4$, $S_5$, $S_6$, $S_7$} and Σ={F, Y, L} and that five amino acids in the sequences in the MSA 210 at position 1 are F for sequences $S_1$, $S_2$, $S_4$, $S_5$, and $S_7$, Y for sequence $S_3$, and L for sequence $S_6$.

Per the sequence-to-weight mapping 420 in FIG. 4, it follows that $$f'^F_1 = w_{S_1} + w_{S_2} + w_{S_4} + w_{S_5} + w_{S_7} = \frac{0.3}{7} + \frac{0.4}{7} + \frac{0.6}{7} + \frac{0.7}{7} + \frac{0.9}{7} = \frac{2.9}{7},$$

$$f'^Y_1 = w_{S_3} = \frac{0.5}{7},$$

and $$f'^L_1 = w_{S_6} = \frac{0.8}{7}.$$

Since there are 7 sequences in the MSA 210, the denominator is left as 7 throughout the figures for clarity.

In some implementations, instead of calculating each $w_s$ from the alignments themselves (e.g., via similarity to other sequences), each $w_s$ can be initialized to $$\frac{1}{|S|}$$

before training. The parameters can be left differentiable during training. For example, this means that a model (e.g., PrimateAI, PrimateAI 2D, PrimateAI 3D, JigsawAI) can learn itself how important each of the sequences are as contributors to the phenotype signal of $$f'^A_i.$$

The training process of the species proximity-aware differential weighting logic 430 will be described in detail in accordance with FIG. 7.

The weighted summary statistics disclosed herein can be used to analyze sequences of residues including amino acids, nucleotides, carbohydrates, lipids, or other types of biological polymers. That is, the multiple sequence alignments (MSAs) for which the disclosed weighted summary statistics are generated can include amino acids, nucleotides, carbohydrates, lipids, or other types of biological polymers (e.g., DNA, RNA). Also, each residue can be a position/element in the sequences, which are arranged, for example, as multiple sequence alignments.

In another implementation, a multiple sequence alignment (MSA) aligns a query sequence with a plurality of non-query sequences of a species group that is homologous to the first species. Weights assigned to non-query sequences in the plurality of non-query sequences can be proportional to a degree of homology between the first species and species in the species group. The degree of homology can be measured by i) an evolutionary distance between the first species and the species in the species group, and/or ii) a number of mismatches between the query sequence and the non-query sequences, and/or iii) chemical similarity of the residues.

Homology, in biology, refers to the similarity of the structure, physiology, or development of different species of organisms based upon their descent from a common evolutionary ancestor. Homology is contrasted with "analogy," which is a functional similarity of structure-based not upon common evolutionary origins but upon similar environmental benefit and functional usage. Thus, the forelimbs of such widely differing mammals as humans, bats, and deer are homologous; the form of construction and the number of bones in these varying limbs are practically identical and represent adaptive modifications of the forelimb structure of their common early mammalian ancestors. Analogous structures, on the other hand, can be represented by the wings of birds and of insects; the structures are used for flight in both types of organisms, but they have no common ancestral origin at the beginning of their evolutionary development.

The query sequence can belong to a human. The non-query sequences can belong to other humans and/or non-human primates. Those species in the species group that are evolutionarily proximate to the first species can be assigned greater weights than those species in the species group that are evolutionarily distant from the first species. The greater weights can cause the species in the species group that are evolutionarily proximate to the first species to contribute more respectively to the weighted summary statistic than the species in the species group that are evolutionarily distant from the first species.

In other implementations, the query sequence can be assigned a maximum weight. In some implementations, the phenotyping logic 170 (FIG. 1) can be used as a proxy for a weighted contribution of a non-query sequence to evolutionary constraint of a variant in the query sequence in place of the training process to learn the respective weighted contribution, as described in FIG. 1.

Technical Application—Examples of Phenotype Prediction

Figure 5:
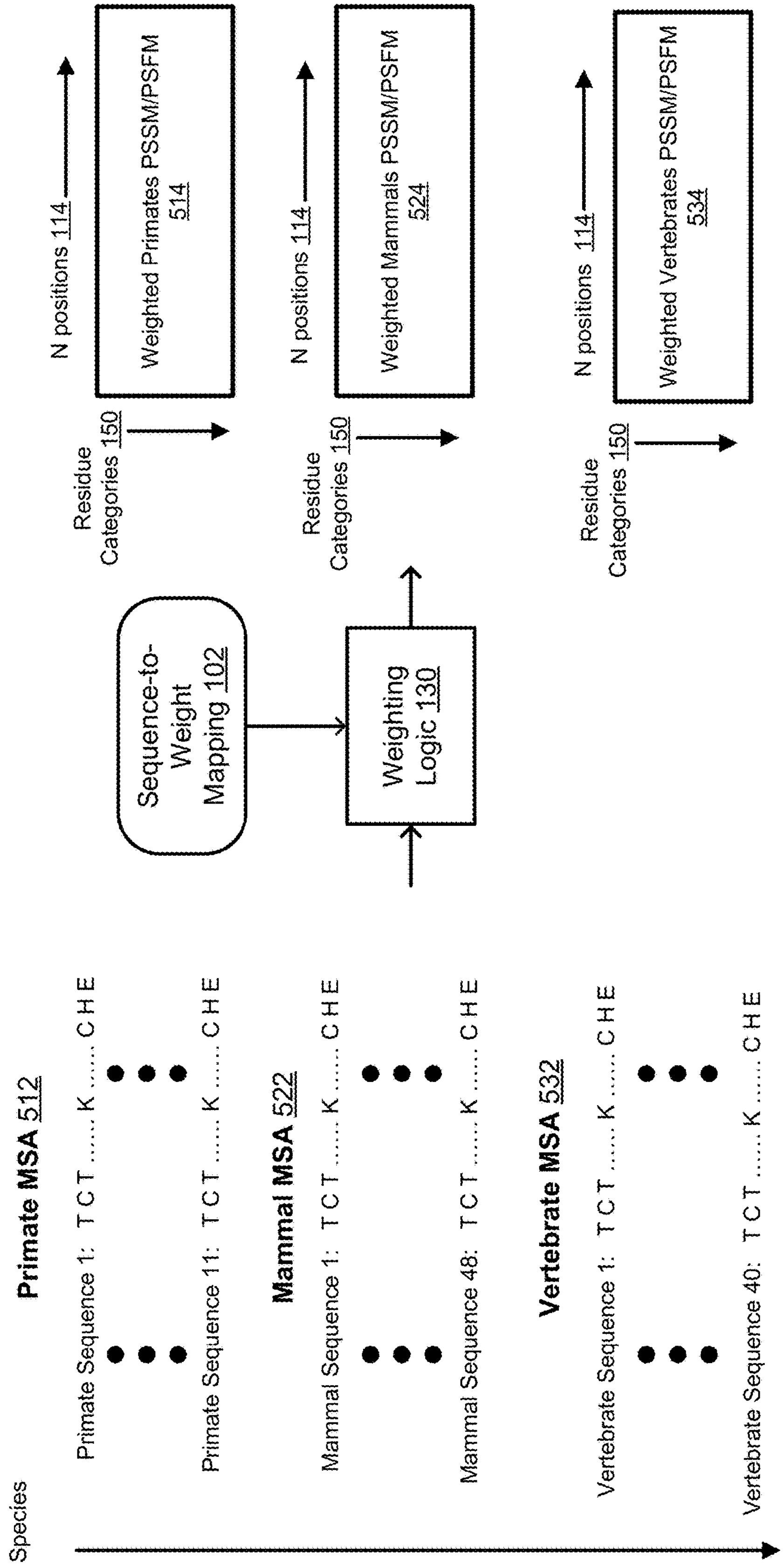
FIG. 5 shows implementations of weighted evolutionary profiles for primate, mammal, and vertebrate MSAs, respectively.

FIG. 5 shows one implementation of weighted evolutionary profile 500 technology disclosed. The weighted primate, mammal, and vertebrate evolutionary profiles 514, 524, and 534 for primate, mammal, and vertebrate MSAs 512, 522, and 532 are generated. Multiple profiles or a single profile can be created. In FIG. 5, the weighted primate, mammal, and vertebrate evolutionary profiles 514, 524, and 534 are collectively referred to as weighted evolutionary profiles 504. The primate, mammal and vertebrate MSAs 512, 522 and 532, respectively, are across multiple species. For example, the primate MSA 512 can include 11 primate sequences, the mammal MSA 522 can include 48 mammal sequences excluding primates and the vertebrate MSA can include 40 vertebrate sequences excluding primates and mammals. The weighting logic 130 can have access to the sequence-to-weight mapping 102 and determine the weighted evolutionary profiles 504, in which the evolutionary conservation scores or frequencies are differentially weighted according to weights assigned to underlying sequences by the sequence-to-weight mapping 102. Each of the weighted primate, mammal, and vertebrate evolutionary profiles 514, 524, and 534 can be in a matrix form of residue categories 150 (e.g., twenty-one amino acid categories (including stop or gap amino acid category)) at N positions 114.

Figure 6:
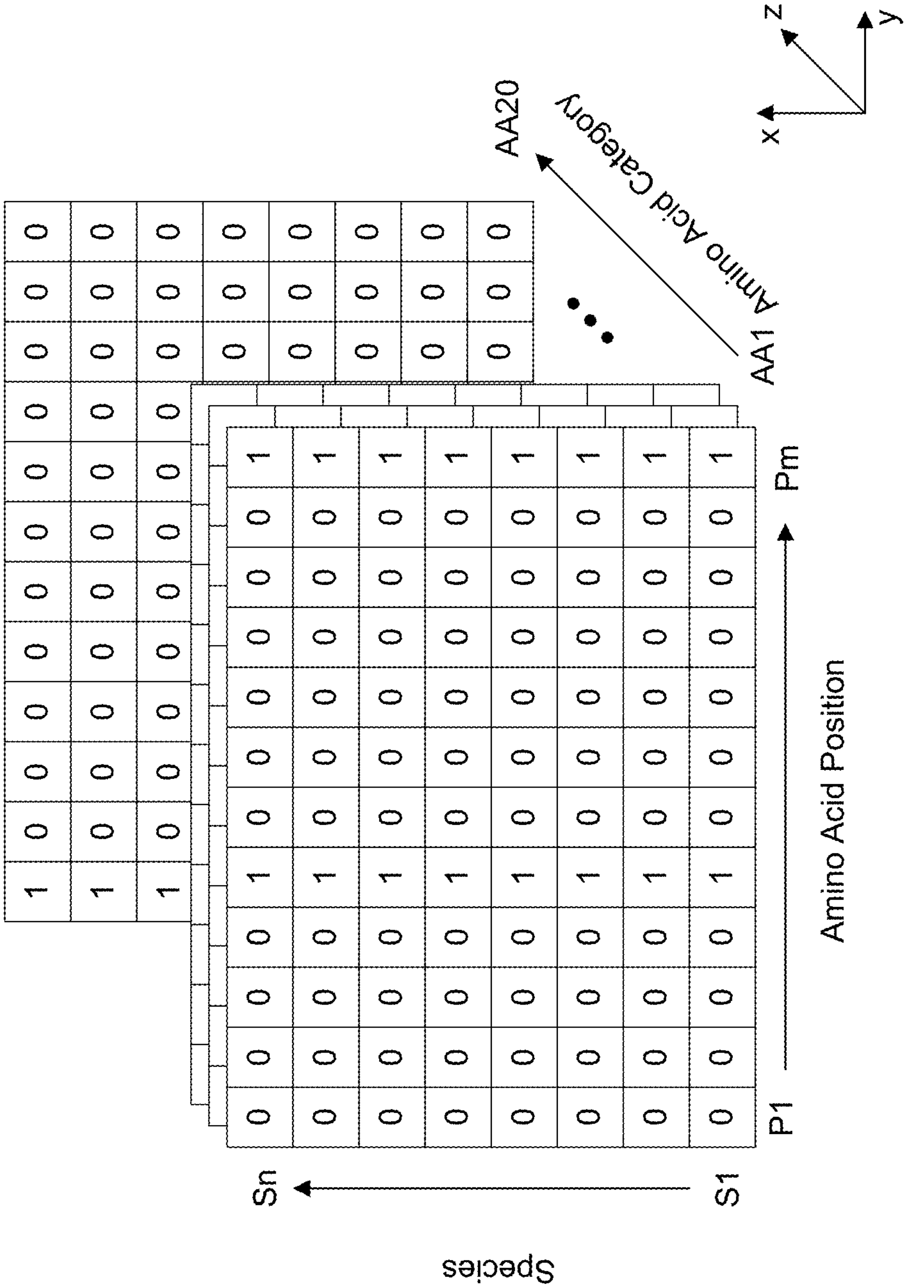
FIG. 6 depicts one implementation of one-hot encoded MSA over multiple species used as input to the weighting logic to generate weighted evolutionary profiles with species-specific weights.

When MSAs are input to the weighting logic, they can be one-hot encoded. FIG. 6 depicts one implementation of one-hot encoded MSA used as input to the weighting logic to generate weighted evolutionary profiles with species-specific weights. The input can be in a three-dimensional form, with a size of |S|*|P|*20, where S is the number of species and P is the amino acid position. As illustrated, the x-axis lists different species from S1 to Sn, where n is the number of species. For example, the species can include 99 species from primate, mammal and vertebrate (n=99). The y-axis is amino acid position from P1 to Pm in an amino acid sequence, where m is the length of the amino acid sequence. For example, an average length of human proteins is 472 amino acids (m=472). The z-axis is the amino acid category from AA1 to AA20 as there are twenty types of amino acids. In one embodiment, the amino acid categories can be 21, representing twenty amino acid categories and one stop or gap amino acid category. For each of the amino acid positions, a particular amino acid (element) can be encoded as “1” and the other elements encoded as “0”. For a particular amino acid category AA1, for example, all the species have AA1 at both amino acid positions P5 and Pm.

As another example, the multiz100 alignments cover the entire human proteome, as they come from a whole-genome DNA-level MSA. The MSA can be three billion positions long, because there are three billion DNA positions in the human genome.

The weighting logic can process the three-dimensional one-hot encoded MSA and generate two-dimensional weighted evolutionary profiles as output. As illustrated in FIG. 5, for example, the weighted evolutionary profiles 504, including weighted primate, mammal and vertebrate PSSM/PSFM 514, 524 and 534, can be in the two-dimensional form of N positions 114 and residue categories 150.

Figure 7:
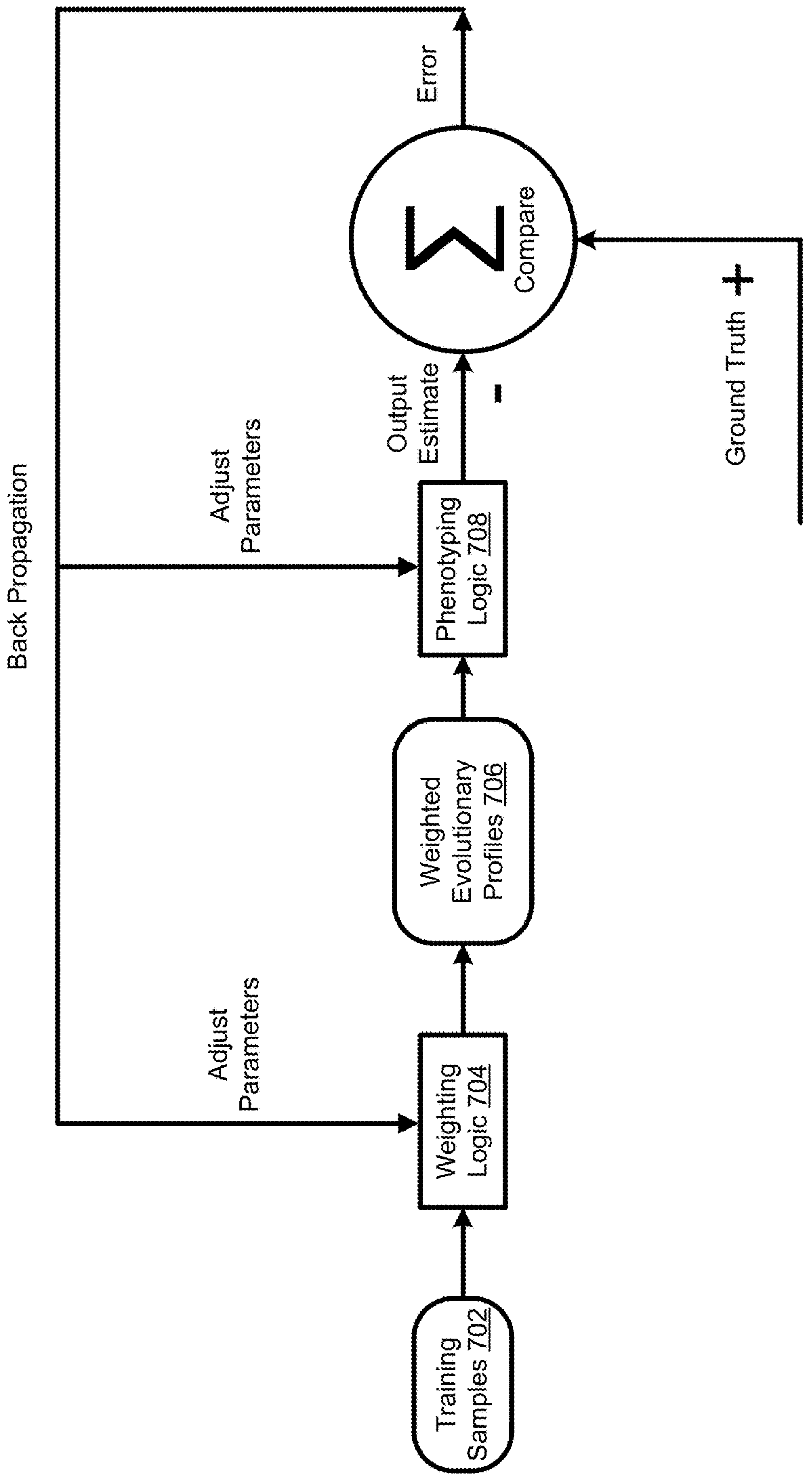
FIG. 7 depicts one implementation of training the weighting logic along with phenotyping logic through backpropagation.

FIG. 7 depicts one implementation of training the weighting logic along with phenotyping logic through backpropagation. The weighting logic 704 (e.g., weighting logic 130 and species proximity-aware differential weighting logic 430) processes training samples 702 as input and generates weighted evolutionary profiles 706, with species-specific weights. The training samples can include a subset of labelled human protein variants. In accordance with FIG. 6, the training samples can be in a three-dimensional form of one-hot encodings of MSAs using multiple species. The generated weighted evolutionary profiles 706 are fed to the phenotyping logic 708 (e.g., PrimateAI, PrimateAI 2D, PrimateAI 3D, JigsawAI described below in FIGS. 8-12), which in turn generates predicted pathogenicity of the labeled human protein variants.

The parameters of the weighting logic 704 including species-specific weights, and parameters of the phenotyping logic 708 can be optimized during training via backpropagation. During training, the weighting logic 704 and phenotyping logic 708 gradually combines simpler features into complex features so that the most suitable hierarchical representations can be learned from training samples. The forward pass sequentially computes the output and propagates the function signals forward through the weighting logic 704 and phenotyping logic 708. In the final output layer, an objective loss function measures error between the estimated outputs and the given labels of the training samples. To minimize the training error, the backward pass uses the chain rule to backpropagate error signals and compute gradients with respect to all parameters throughout the weighting logic 704 and phenotyping logic 708. Finally, the parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Figure 8:
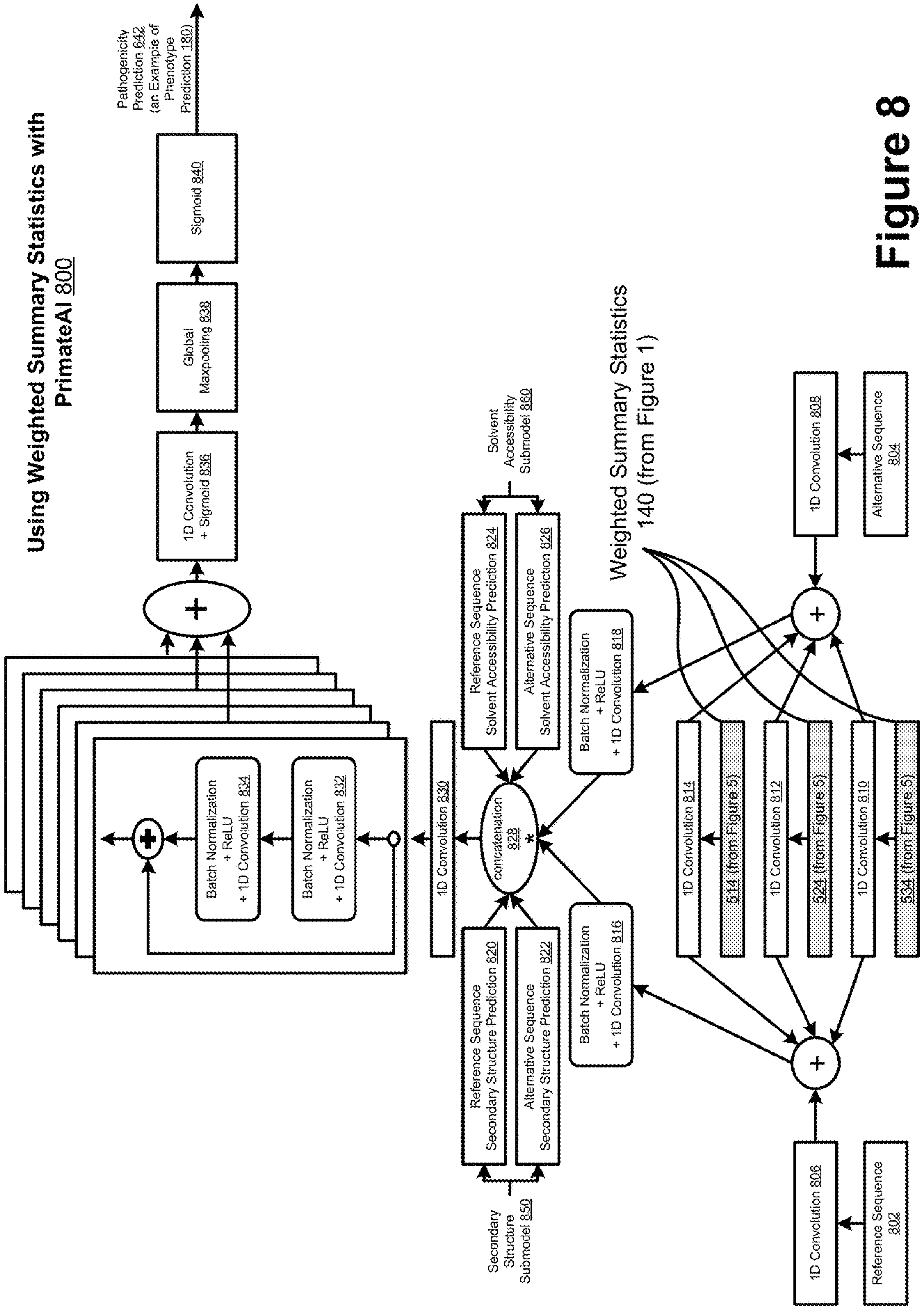
FIG. 8 depicts one implementation of using weighted summary statistics, generated in accordance with one implementation of the technology disclosed, as input to the pathogenicity classifier for variant pathogenicity prediction.

FIG. 8 depicts one implementation 800 of using weighted summary statistics, generated in accordance with one implementation of the technology disclosed, as input to a pathogenicity classifier (e.g., PrimateAI model) for variant pathogenicity prediction. In particular, the inputs to a convolutional neural network of the PrimateAI model include a reference sequence 802 and an alternative sequence 804 with a variant, conservation represented by the weighted primate, mammal, and vertebrate summary statistics 514, 524 and 534, the reference and alternative sequences secondary structure predictions 820 and 822 of a pre-trained secondary structure sub-model 850, as well as the reference and alternative sequences solvent accessibility predictions 824 and 826 of a pre-trained solvent accessibility sub-model 860. The reference sequence 802, the alternative sequence 804, the weighted primate, mammal, and vertebrate evolutionary profiles 514, 524, and 534 are direct inputs to the PrimateAI model. The secondary structure predictions 820 and 822 of the reference and alternative sequences, as well as the solvent accessibility predictions 824 and 826 of the reference and alternative sequences are indirect input to the PrimateAI model.

The secondary structure and solvent accessibility sub-models 850 and 860 are pre-trained on known protein crystal structures for the Protein DataBank, and allow backpropagation during the pathogenicity model training. The pre-trained secondary structure sub-model 850 is used to generate secondary structure predictions of the reference and alternative sequences, namely, 3-state secondary structures of alpha helix (H), beta sheet (B), and coils (C). The pretrained solvent accessibility sub-model 860 is used to generate solvent accessibility predictions of the reference and alternative sequences, namely, 3-state solvent accessibility: buried (B), intermediate (I), and exposed (E). For each amino acid residue within the reference and alternative sequences, the secondary structure and solvent accessibility sub-models predict one state of secondary structure and one state of solvent accessibility, respectively.

The reference sequence 802 and alternative sequence 804 are passed through 1D convolution layers 806 and 808, respectively, to generate respective feature map. Similarly, the weighted primate, mammal, and vertebrate evolutionary profiles 514, 524, and 534 are also passed through 1D convolution layers 810, 812 and 814, respectively, to generate respective feature maps. The feature map of the reference sequence 802 is merged with the three types of weighted evolutionary profile feature maps, followed by batch normalization with the activation of ReLU and passing through 1D convolution (see 816). The feature map of the alternative sequence 804 is merged with the three types of weighted evolutionary profile feature maps, followed by batch normalization with the activation of ReLU and passing through 1D convolution (see 818). The merged feature map corresponding to the reference sequence 802 and the merged feature map corresponding to the alternative sequence 804 are subsequently concatenated with the reference sequence secondary structure prediction 820, the alternative sequence secondary structure prediction 822, the reference sequence solvent accessibility prediction 824 and the alternative sequence solvent accessibility prediction 826 (see 828). The concatenated features are passed through 1D convolution 830 and groups of residual blocks with convolution filters having the same convolution window size, batch normalization and ReLU layers (see 832 and 834). In one embodiment, the last three residual blocks have an atrous rate of 2 for the 1D convolutions, to give higher coverage for the kernels. The output generated from the groups of residual blocks is passed through 1D convolution and activation sigmoid 836, followed by a global maxpooling 838 and sigmoid 840. The generated output represents the pathogenicity prediction 842 of the variant (i.e., an example of phenotype prediction 180).

Additional details about various embodiments of the PrimateAI model can be found in Sundaram, L. et al. Predicting the clinical impact of human mutation with deep neural networks. *Nat. Genet.* 50, 1161-1170 (2018); US Patent Application Nos. 62/573,144; 62/573,149; 62/573,153; 62/582,898; 16/160,903; 16/160,986; 16/160,968; and Ser. No. 16/407,149, which are incorporated herein by reference as if fully set forth herein. Further particular implementations of the disclosed system and inputs for the PrimateAI model are described further below under 'Particular Implementations'.

Figure 9:
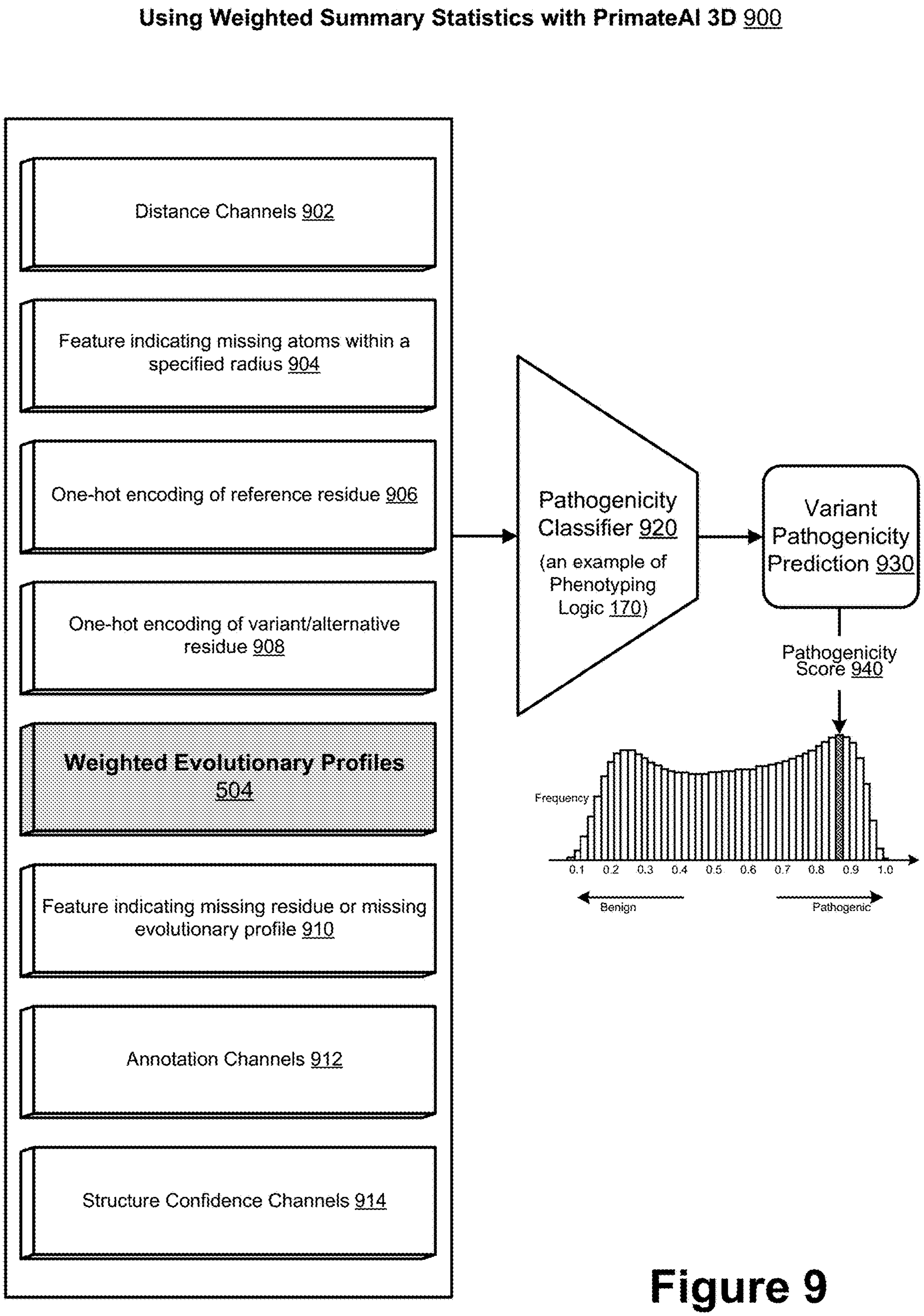
FIG. 9 depicts one implementation of using weighted summary statistics, generated in accordance with one implementation of the technology disclosed, as input to the pathogenicity classifier for variant pathogenicity prediction.

FIG. 9 depicts one implementation 900 of using weighted summary statistics, generated in accordance with one implementation of the technology disclosed, as input to the PrimateAI 3D model for variant pathogenicity prediction. In particular, the weighted evolutionary profiles 504 are used as inputs to the PrimateAI 3D model. As illustrated, different combinations and permutations of input channels that can be provided as inputs to a pathogenicity classifier 920 for pathogenicity prediction 930 of a target variant, by generating a pathogenicity score 940. For example, a low pathogenicity score 940 can indicate the variant is benign and a high score indicate the variant is pathogenic. The pathogenicity classifier 920 can be an example of phenotyping logic 170.

Another one of the inputs can be distance channels 902. In one implementation, three-dimensional protein structures are represented using voxels in a voxel grid. The voxels in the voxel grid have a plurality of distance channels (e.g., twenty-one distance channels for the twenty-one amino acid categories, respectively (including stop or gap amino acid category)). The distance channels 902 can be independently generated for each of the twenty-one amino acid categories. Consider, for example, the Alanine (A) amino acid category. Further consider, for example, that the voxel grid is of size 3×3×3 and has twenty-seven voxels. Then, in one implementation, an Alanine distance channel includes twenty-seven distance values for the twenty-seven voxels in the voxel grid, respectively. The twenty-seven distance values in the Alanine distance channel are measured from respective centers of the twenty-seven voxels in the voxel grid to respective nearest atoms in the Alanine amino acid category. In other implementations, the distance channels 902 are generated based on distances between voxel centers and atoms across a plurality of atomic elements irrespective of amino acids.

In some implementations, the distances are normalized by a maximum scan radius to generate normalized distances. In another implementation, the distance channels 902 are generated based on distances between voxel centers and alpha-carbon atoms on an amino acid-basis. In some implementations, the distances are normalized by the maximum scan radius to generate normalized distances. In yet another implementation, the distance channels 902 are generated based on distances between voxel centers and beta-carbon atoms on an amino acid-basis. In some implementations, the distances are normalized by the maximum scan radius to generate normalized distances. In yet another implementation, the distance channels 902 are generated based on distances between voxel centers and side chain atoms on an amino acid-basis. In some implementations, the distances are normalized by the maximum scan radius to generate normalized distances. In yet another implementation, the distance channels 902 are generated based on distances between voxel centers and backbone atoms on an amino acid-basis. In some implementations, the distances are normalized by the maximum scan radius to generate normalized distances. In yet another implementation, the distance channels 902 are generated based on distances (one feature) between voxel centers and the respective nearest atoms irrespective of atom type and amino acid type. In yet another implementation, the distance channels are generated based on distances (one feature) between voxel centers and atoms from non-standard amino acids. In some implementations, the distances between the voxels and the atoms are calculated based on polar coordinates of the voxels and the atoms. The polar coordinates are parameterized by angles between the voxels and the atoms. In one implementation, this angel information is used to generate an angle channel for the voxels (i.e., independent of the distance channels). In some implementations, angles between a nearest atom and neighboring atoms (e.g., backbone atoms) can be used as features that are encoded with the voxels.

Another one of the inputs can be a feature 904 indicating missing atoms within a specified radius.

Another one of the inputs can be one-hot encoding 906 of the reference amino acid. Another one of the inputs can be one-hot encoding 908 of the variant/alternative amino acid.

Another one of the inputs can be a feature 910 indicating missing residue or missing evolutionary profile.

Another one of the inputs can be annotations channels 912 generated by an annotations generator. In one implementation, the annotations channels 912 can be generated based on molecular processing annotations. In another implementation, the annotations channels 912 can be generated based on regions annotations. In yet another implementation, the annotations channels 912 can be generated based on sites annotations. In yet another implementation, the annotations channels 912 can be generated based on amino acid modifications annotations. In yet another implementation, the annotations channels 912 can be generated based on secondary structure annotations. In yet another implementation, the annotations channels 912 can be generated based on experimental information annotations.

Another one of the inputs can be structure confidence channels 914 generated by a structure confidence generator. In one implementation, the structure confidence 914 can be generated based on global model quality estimations (GMQEs). In another implementation, the structure confidence 914 can be generated based on qualitative model energy analysis (QMEAN) scores. In yet another implementation, the structure confidence channels 914 can be generated based on template modeling scores. Examples of the template modeling scores can include minimum template modeling scores, mean template modeling scores, and maximum template modeling scores.

A person skilled in the art will appreciate that any permutation and combination of the input channels can be concatenated into an input for processing through the pathogenicity classifier 920 for the pathogenicity prediction 930 of the target variant. In some implementations, only a subset of the input channels may be concatenated. The input channels can be concatenated in any order. In one implementation, the input channels can be concatenated into a single tensor by a tensor generator (input encoder). This single tensor can then be provided as input to the pathogenicity classifier 920 for the pathogenicity prediction 930 of the target variant.

Additional details about the PrimateAI 3D model can be found in U.S. patent application Ser. No. 17/232,056; 63/175,495; 63/175,767; and Ser. No. 17/468,411, which are incorporated herein by reference as if fully set forth herein.

Figure 10:
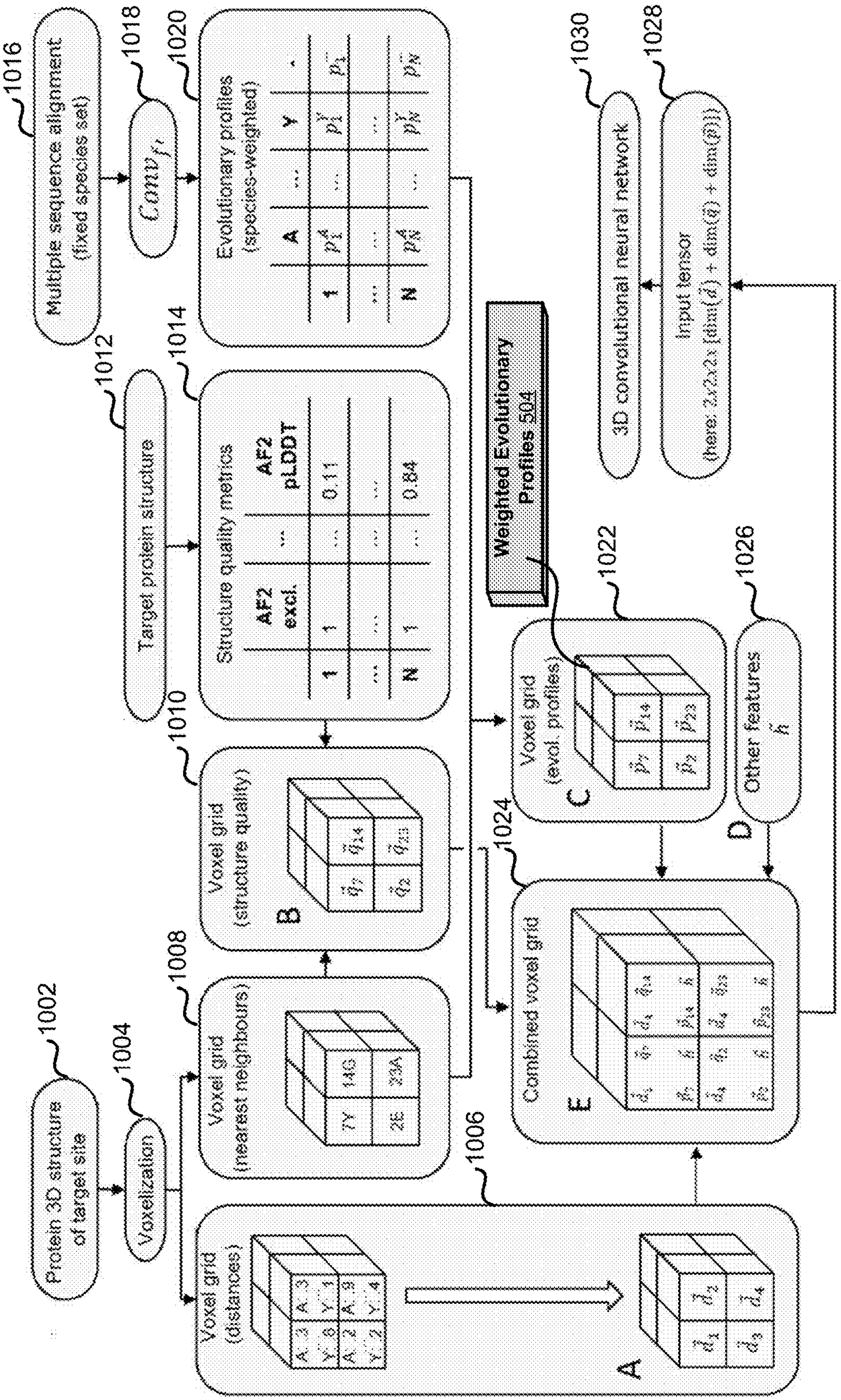
FIG. 10 is a voxelized depiction of FIG. 9.

FIG. 10 is a voxelized depiction of FIG. 9. In particular, the three-dimensional (3D) structure 1002 of a target protein with a target amino acid site is represented by voxels in a voxel grid via voxelization 1004. For example, the voxel grid can be of size 2×2×2 and has eight voxels. Like the Alanine distance channel as described above, the distance channel generator can generate a distance channel (i.e., a set of voxel-wise distance values) for each of the amino acid categories. The nearest neighbors of the target site can also be represented by voxels 1008 in the voxel grid, which are used along with the structure quality metrics 1014 of the structure 1012 of the target protein, to generate voxelized structure quality 1010. The MSA with fixed species set 1016 can be convoluted via convolution 1018 to generate species-weighted evolutionary profiles 1020, which in turn can be used to generate voxelized weighted evolutionary profiles 1022 (representing weight evolutionary profiles 504). The voxelized distances 1006 ($\vec{d}$), voxelized structure quality of the target protein 1010 ($\vec{q}$), voxelized weighted evolutionary profiles 1022 ($\vec{d}$), along with other features 1026 ($\vec{h}$) can be merged into a combined voxel grid 1024 and concatenated into input tensor 1028 (e.g., 2×2×2 [dim($\vec{d}$)+dim($\vec{q}$)+dim($\vec{p}$)]). The input tensor 1028 can be used as input and fed to a 3D convolutional neural network-based pathogenicity classifier 1030.

Figure 11:
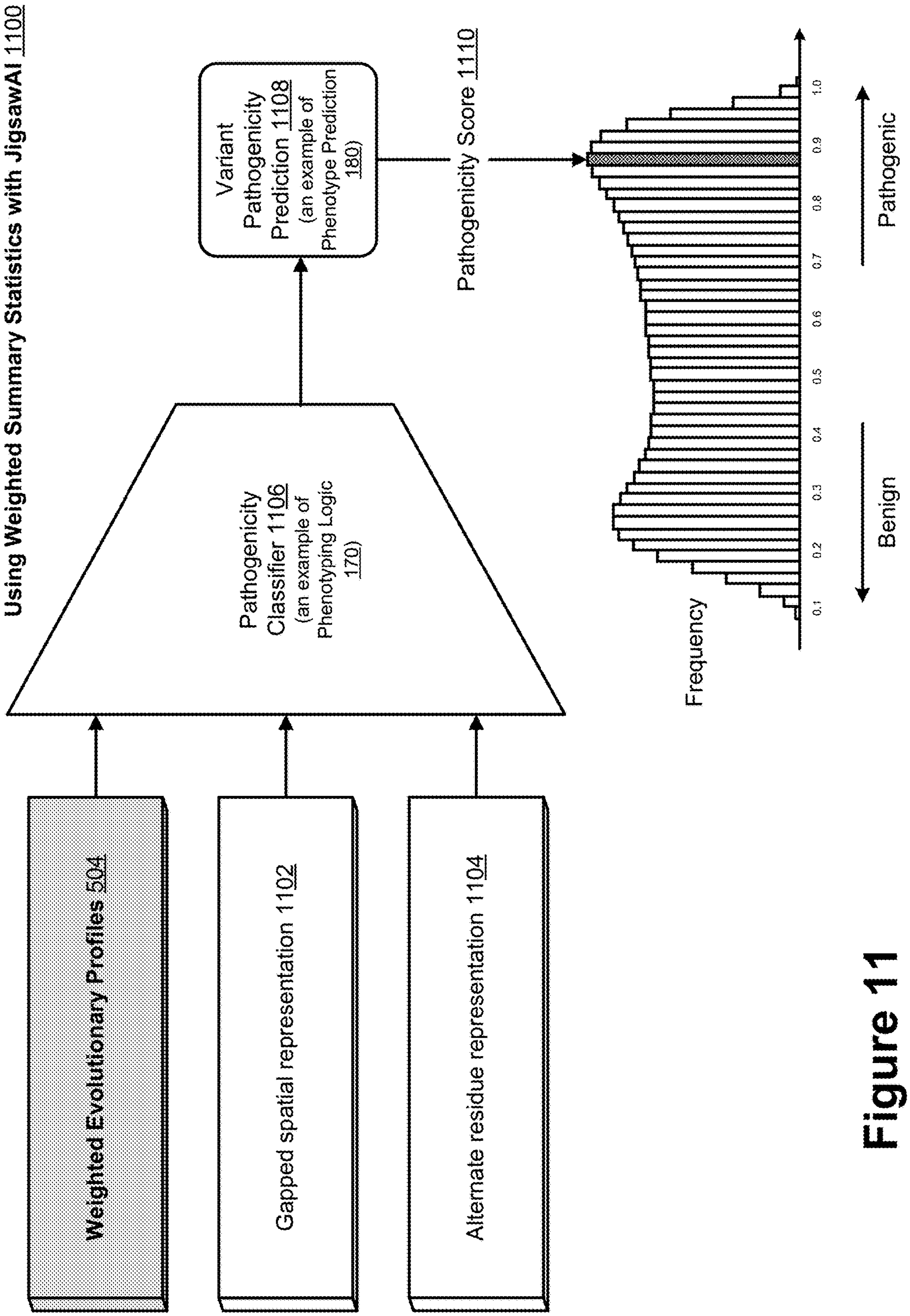
FIG. 11 depicts one implementation of using weighted summary statistics, generated in accordance with one implementation of the technology disclosed, as input to the pathogenicity classifier for variant pathogenicity prediction.

FIG. 11 depicts one implementation 1100 of using weighted summary statistics, generated in accordance with one implementation of the technology disclosed, as input to the pathogenicity classifier (e.g., JigsawAI model) for variant pathogenicity prediction. In particular, the weighted evolutionary profiles 504 are used as one of the inputs to the pathogenicity classifier 1106, which in turn generates the pathogenicity prediction 1108 of the variant, by generating a pathogenicity score 1110. As illustrated, different combinations and permutations of input channels that can be provided as inputs to the pathogenicity classifier 1106 for pathogenicity prediction 1108 of a target variant, by generating the pathogenicity score 1110. For example, a low pathogenicity score 1110 can indicate the variant is benign and a high score indicate the variant is pathogenic. The pathogenicity classifier 1106 is an example of phenotyping logic 170, and the variant pathogenicity prediction 1108 is an example of phenotyping prediction 180.

Another input to the pathogenicity classifier 1106 is gapped spatial representation 1102 of a target protein. The "gaped spatial representation" of a protein is such a spatial representation of the protein that excludes at least one gap amino acid in the protein. In one implementation, a gap amino acid is excluded by excluding (or not considering or ignoring) one or more atoms or atom-types of the gap amino acid when generating the gaped spatial representation. For example, the atoms of the gap amino acid can be excluded from the calculations (or selections or computations) that produce the distance channels, the evolutionary profiles, the annotation channels, and/or the structure confidence channels. In other implementations, the gaped spatial representation can be generated by excluding the gap amino acid from other feature channels as well.

The spatial configurations of non-gap amino acids can be encoded as amino acid class-wise distance channels. Each of the amino acid class-wise distance channels has voxel-wise distance values for voxels in a plurality of voxels. The voxel-wise distance values specify distances from corresponding voxels in the plurality of voxels to atoms of the non-gap amino acids. The spatial configurations of the non-gap amino acids are determined based on spatial proximity between the corresponding voxels and the atoms of the non-gap amino acids. The spatial configuration of a gap amino acid is excluded from the gapped spatial representation by disregarding distances from the corresponding voxels to atoms of the gap amino acid when determining the voxel-wise distance values. The spatial configuration of the gap amino acid is excluded from the gaped spatial representation by disregarding spatial proximity between the corresponding voxels and the atoms of the gap amino acid.

Another input to the pathogenicity classifier 1106 is alternate residue representation 1104. An alternative residue (amino acid) can be generated by a nucleotide variant at a particular position. In some implementations, the alternate amino acid is an amino acid that is same as a reference amino acid. In other implementations, the alternate amino acid is an amino acid that is different from the reference amino acid. The representation of the alternate amino acid can be a voxelized one-hot encoding of the alternate amino acid. The voxelized dimensionality of the voxelized one-hot encoded alternate residue (amino acid) can be 21×1×1×1, where 21 denotes the twenty-one amino acid categories including 20 types of amino acids and 1 stop or gap amino acid category.

Additional details about the JigsawAI model can be found in 63/253,122; 63/281,579; 63/281,592; 17/533,091, which are incorporated herein by reference as if fully set forth herein.

Figure 12:
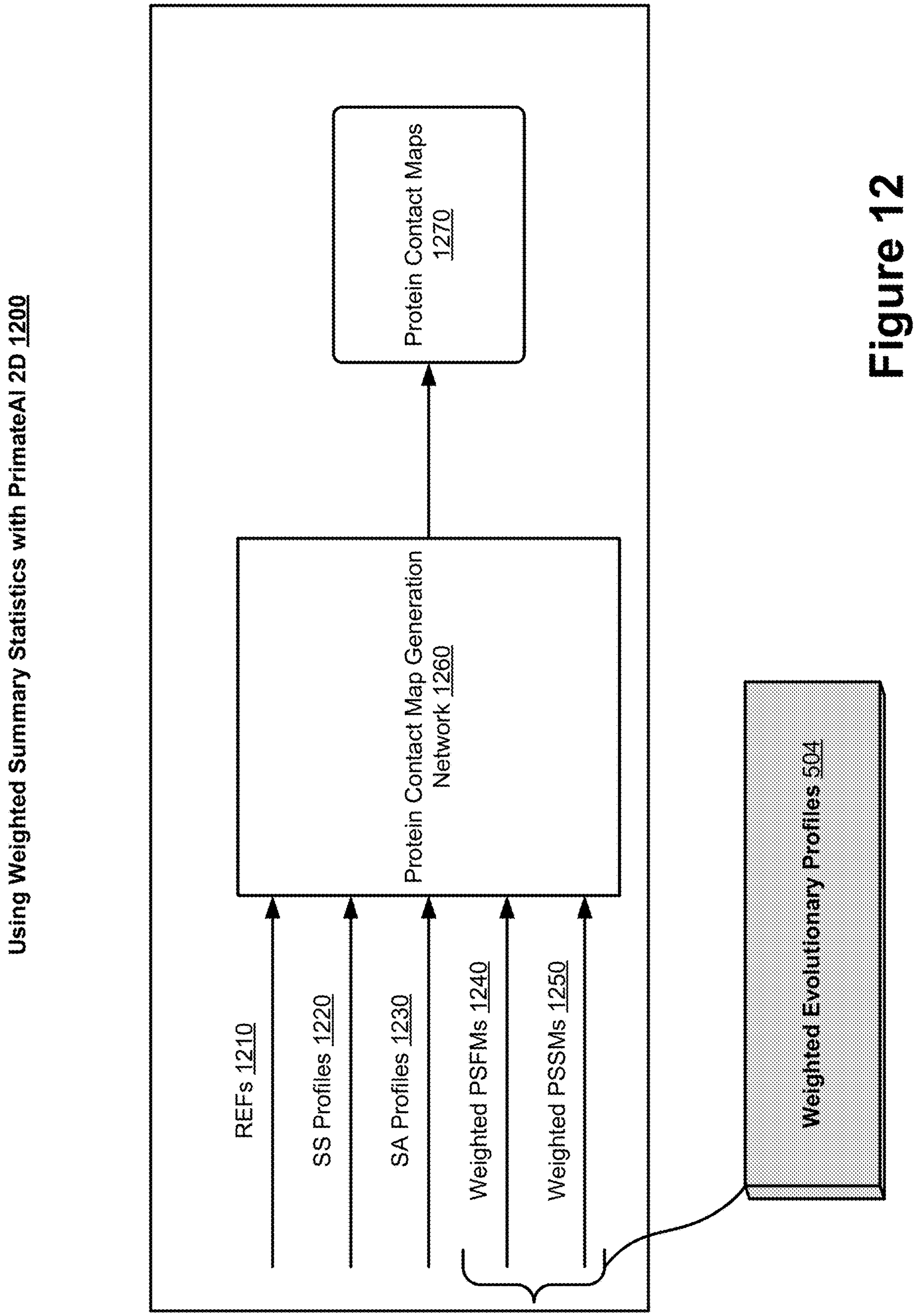
FIG. 12 depicts one implementation of using weighted summary statistics, generated in accordance with one implementation of the technology disclosed, as input to the protein contact map generation network for protein contact map generation.

FIG. 12 depicts one implementation 1200 of using weighted summary statistics, generated in accordance with one implementation of the technology disclosed, as input to the protein contact map generation network 1260 (e.g., PrimateAI 2D model) for protein contact map generation. The protein contact map generation network 1260 is trained to process, as input, at least one of: (i) reference amino acid sequences (REFs) 1210 of proteins, (ii) secondary structure (SS) profiles 1220 of the proteins, (iii) solvent accessibility (SA) profiles 1230 of the proteins, (iv) weighted position-specific frequency matrices (PSFMs) 1240 of the proteins, and (v) weighted position-specific scoring matrices (PSSMs) 1250 of the proteins, and generate, as output, protein contact maps 1270.

Protein contact maps 1270 represent the distance between all possible amino acid residue pairs of a 3D protein structure using a binary two-dimensional matrix. For two residues i and j, for example, the $ij^{th}$ element of the matrix is 1 if the two residues are closer than a predetermined threshold, and 0 otherwise. Various contact definitions have been proposed—the distance between the Cα-Cα atom with threshold 6-12 Å; distance between Cβ-Cβ atoms with threshold 6-12 Å (Cα is used for Glycine); and distance between the side-chain centers of mass.

Protein contact maps provide a more reduced representation of a protein structure than its full 3D atomic coordinates. The advantage is that protein contact maps are invariant to rotations and translations, which makes them more easily predictable by machine learning methods. It has also been shown that under certain circumstances (e.g., low content of erroneously predicted contacts) it is possible to reconstruct the 3D coordinates of a protein using its protein contact map. Protein contact maps are also used for protein superimposition and to describe similarity between protein structures. They are either predicted from protein sequence or calculated from a given structure.

A protein contact map describes the pairwise spatial and functional relationship of amino acids (residues) in a protein and contains key information for protein 3D structure prediction. In some implementations, two residues of a protein are in contact if their Euclidean distance is <8 Å. The distance of two residues can be calculated using Cα or Cβ atoms, corresponding to Cα- or Cβ-based contacts. A protein contact map can also be considered a binary L×L matrix, where L is the protein length. In this matrix, an element with value 1 indicates the corresponding two residues are in contact; otherwise, they are not in contact.

Additional details about the PrimateAI 2D model can be found in U.S. Patent Application No. 63/229,897, which is incorporated herein by reference as if fully set forth herein.

In one implementation of the technology disclosed, the number of convolutional filters can be increased to generate multiple alternative frequency profiles from the same alignments. In another implementation, the kernel size can be increased to calculate frequencies of multiple protein sites at a time in tandem. In some implementations, activation functions can be added after each convolution and stack layers to introduce non-linearities between species.

Computer System

Figure 13:
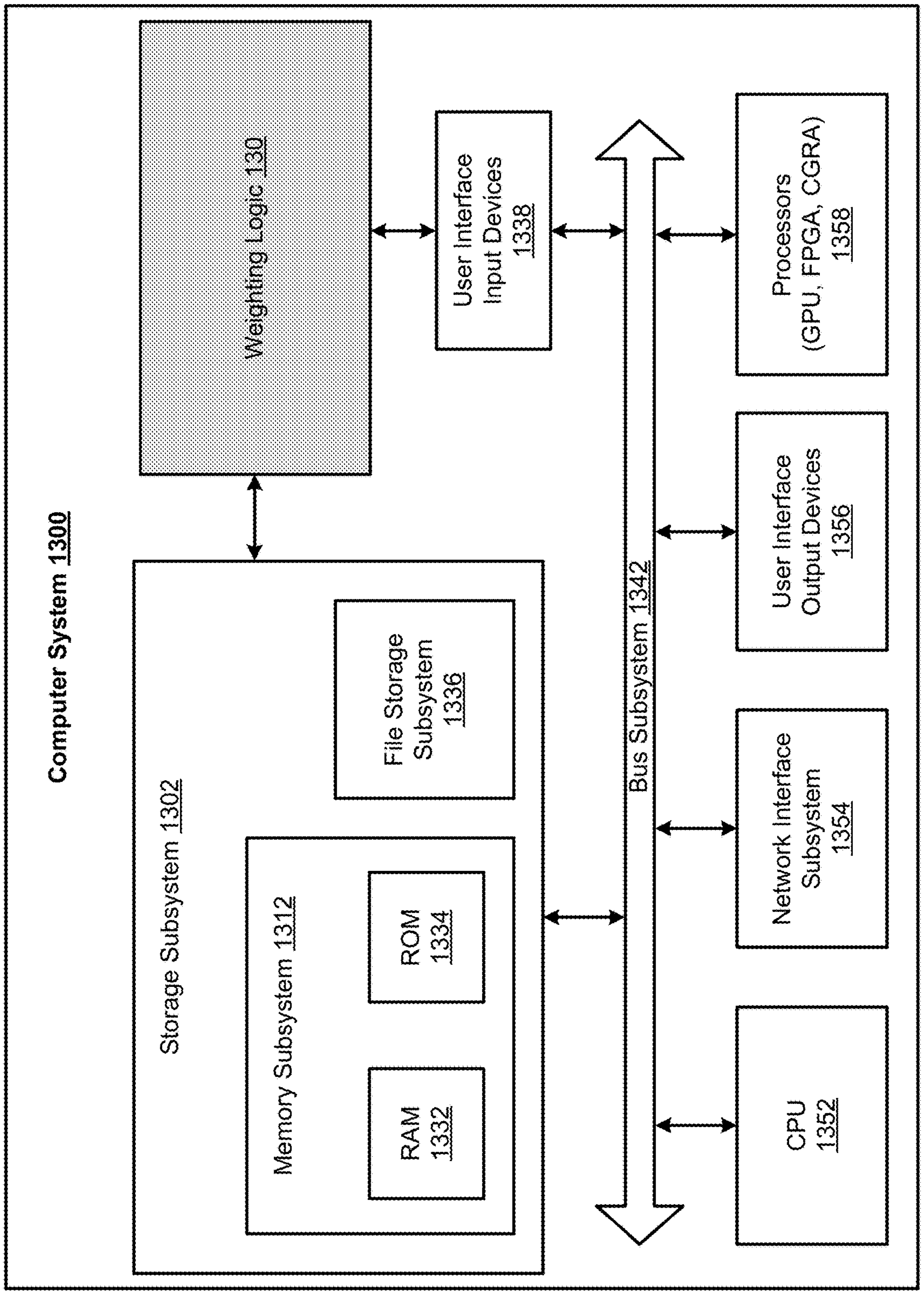
FIG. 13 shows an example computer system that can be used to implement the technology disclosed.

FIG. 13 shows an example computer system 1300 that can be used to implement the technology disclosed. Computer system 1300 includes at least one central processing unit (CPU) 1352 that communicates with a number of peripheral devices via bus subsystem 1342. These peripheral devices can include a storage subsystem 1302 including, for example, a memory subsystem 1312 and a file storage subsystem 1336, user interface input devices 1338, user interface output devices 1356, and a network interface subsystem 1354. The input and output devices allow user interaction with computer system 1300. Network interface subsystem 1354 provides an interface to outside networks, including an interface to corresponding interface devices in other computer systems.

In one implementation, the weighting logic 130 is communicably linked to the storage subsystem 1302 and the user interface input devices 1338.

User interface input devices 1338 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1300.

User interface output devices 1356 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1300 to the user or to another machine or computer system.

Storage subsystem 1302 stores programming and data constructs that provide the functionality of some or all of the modules and methods described herein. These software modules are generally executed by processors 1358.

Processors 1358 can be graphics processing units (GPUs), field-programmable gate arrays (FPGAs), application-specific integrated circuits (ASICs), and/or coarse-grained reconfigurable architectures (CGRAs). Processors 1358 can be hosted by a deep learning cloud platform such as Google Cloud Platform™, Xilinx™, and Cirrascale™. Examples of processors 1078 include Google's Tensor Processing Unit (TPU)™, rackmount solutions like GX4 Rackmount Series™, GX10 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 1312 used in the storage subsystem 1302 can include a number of memories including a main random access memory (RAM) 1332 for storage of instructions and data during program execution and a read only memory (ROM) 1334 in which fixed instructions are stored.

A file storage subsystem 1336 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1336 in the storage subsystem 1302, or in other machines accessible by the processor.

Bus subsystem 1342 provides a mechanism for letting the various components and subsystems of computer system 1300 communicate with each other as intended. Although bus subsystem 1342 is shown schematically as a single bus, alternative implementations of the bus subsystem can use multiple busses.

Computer system 1300 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1300 depicted in FIG. 13 is intended only as a specific example for purposes of illustrating the preferred implementations of the present invention. Many other configurations of computer system 1300 are possible having more or less components than the computer system depicted in FIG. 13.

Particular Implementations

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and features of the technology disclosed or elements thereof can be implemented in the form of a computer product, including a non-transitory computer readable storage medium with computer usable program code for performing the method steps indicated. Furthermore, one or more implementations and features of the technology disclosed or elements thereof can be implemented in the form of an apparatus including a memory and at least one processor that is coupled to the memory and operative to perform exemplary method steps. Yet further, in another aspect, one or more implementations and features of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The features described in this section can be combined as features. In the interest of conciseness, the combinations of features are not individually enumerated and are not repeated with each base set of features. The reader will understand how features identified in the features described in this section can readily be combined with sets of base features identified as implementations in other sections of this application. These features are not meant to be mutually exclusive, exhaustive, or restrictive; and the technology disclosed is not limited to these features but rather encompasses all possible combinations, modifications, and variations within the scope of the claimed technology and its equivalents.

Other implementations of the features described in this section can include a non-transitory computer readable storage medium storing instructions executable by a processor to perform any of the features described in this section. Yet another implementation of the features described in this section can include a system including memory and one or more processors operable to execute instructions, stored in the memory, to perform any of the features described in this section.

In one implementation, the technology disclosed describes a system. The system comprises a memory that stores a sequence-to-weight mapping. The sequence-to-weight mapping assigns respective weights to respective sequences in a multiple sequence alignment. The multiple sequence alignment can align a hundred to five hundred sequences, in some implementations, and even more sequences in other implementations.

The system further comprises a weighting logic. The weighting logic has access to the sequence-to-weight mapping. The weighting logic is configured to determine a weighted summary statistic for a given residue category at a given position in the multiple sequence alignment based on one or more weights of one or more sequences in the multiple sequence alignment that have a residue of the given residue category at the given position.

The system further comprises a phenotyping logic. The phenotyping logic is configured to generate a phenotype prediction for the given position based on the weighted summary statistic.

In one implementation, a single sequence in the multiple sequence alignment has the residue of the given residue category at the given position. In such an implementation, the weighted summary statistic is a single weight assigned to the single sequence.

In another implementation, N sequences in the multiple sequence alignment have the residue of the given residue category at the given position. In such an implementation, the weighted summary statistic is a sum of N weights respectively assigned to the N sequences by the sequence-to-weight mapping.

In some implementations, the weighted summary statistic can be a weighted evolutionary profile, for example, a weighted position-specific scoring matrix (wPSSM), or a weighted position-specific frequency matrix (wPSFM). In other implementations, the weighted summary statistic can be a weighted position-specific substitution or conservation frequency. In yet other implementations, the weighted summary statistic can be a weighted position-specific substitution or conservation score.

In some implementations, the multiple sequence alignment aligns a query sequence of a first species with a plurality of non-query sequences of a species group that is homologous to the first species. Weights assigned to non-query sequences in the plurality of non-query sequences can be proportional to a degree of homology between the first species and species in the species group. In one implementation, the degree of homology can be measured by an evolutionary distance between the first species and the species in the species group. In another implementation, the degree of homology can be measured by a number of mismatches between the query sequence and the non-query sequences.

In some implementations, the query sequence belongs to a human, and the non-query sequences belong to non-human primates. Those species in the species group that are evolutionarily proximate to the first species are assigned greater weights than those species in the species group that are evolutionarily distant from the first species. The greater weights cause the species in the species group that are evolutionarily proximate to the first species to contribute more to the weighted summary statistic than the species in the species group that are evolutionarily distant from the first species.

In other implementations, the query sequence is assigned a maximum weight (e.g., 1).

In some implementations, the phenotyping logic can be used as a proxy for a weighted contribution of a non-query sequence to an evolutionary constraint of a variant residue in the query sequence.

As discussed above, the sequence-to-weight mapping assigns the respective weights to the respective sequences in the multiple sequence alignment. In some implementations, the respective weights can be differentiable and learned during a training of the phenotyping logic. The respective weights can be implemented as part of respective convolution filters that are assigned to the respective sequences and are learned during the training of the phenotyping logic.

In some implementations, the sequence-to-weight mapping can assign a plurality of weight sets to a given sequence in the multiple sequence alignment. Weight sets in the plurality of weight sets can be separately applied to generate a plurality of weighted summary statistics for the given sequence. The plurality of weight sets can be implemented as part of a plurality of convolution filters that is assigned to the given sequence and is learned during the training of the phenotyping logic. In some implementations, convolution filters in the plurality of convolution filters can be applied as a convolutional layer, for example, with or without a bias term or an activation function. The convolution filters can also be interspersed with activation functions, and stacked across multiple convolution layers.

In yet other implementations, an increase in a kernel size of a convolution filter in the plurality of convolution filters can cause a determination of multiple weighted summary statistics for multiple positions in the multiple sequence alignment. In yet further implementations, the increase can allow for a determination of multiple weighted summary statistics from a plurality of sequences in the multiple sequence alignment in parallel.

In some implementations, the application of a non-linear activation function following the convolution layer can introduce non-linear relationships between the non-query sequences in the multiple sequence alignment. In some implementations, the application of a plurality of stacked convolution layers in parallel can introduce non-linear relationships between the non-query sequences.

In some implementations, the phenotyping logic can be a variant pathogenicity prediction logic. In other implementations, the phenotyping logic can be a protein contact map generation logic. In yet other implementations, the phenotyping logic can be a protein functionality prediction logic.

In another implementation, the technology disclosed describes a system. The system comprises a memory that stores a sequence-to-weight mapping. The sequence-to-weight mapping assigns respective weights to respective sequences in a multiple sequence alignment. The multiple sequence alignment can align a hundred to five hundred sequences, in some implementations, and even more sequences in other implementations.

The system further comprises a weighting logic. The weighting logic has access to the sequence-to-weight mapping. The weighting logic is configured to determine a weighted summary statistic for a given nucleotide category at a given position in the multiple sequence alignment based on one or more weights of one or more sequences in the multiple sequence alignment that have a nucleotide of the given nucleotide category at the given position.

The system further comprises a phenotyping logic. The phenotyping logic is configured to generate a phenotype prediction for the given position based on the weighted summary statistic.

What is claimed is:

1. A system, comprising:
- at least one processor; and
- a non-transitory computer-readable medium comprising instructions that, when executed by the at least one processor, cause the system to:
  - access a sequence-to-weight mapping stored in memory, wherein the sequence-to-weight mapping assigns respective weights to each non-query sequence in a multiple sequence alignment;
  - based on the sequence-to-weight mapping, determine a weighted summary statistic for a given residue category at a given position in the multiple sequence alignment based on the respective weights for each non-query sequence in the multiple sequence alignment that has a residue of the given residue category at the given position; and
  - generate a phenotype prediction for the given position based on the weighted summary statistic.

2. The system of claim 1, wherein a single sequence in the multiple sequence alignment has the residue of the given residue category at the given position.

3. The system of claim 2, wherein the weighted summary statistic comprises a single weight assigned to the single sequence.

4. The system of claim 1, wherein N sequences in the multiple sequence alignment have the residue of the given residue category at the given position.

5. The system of claim 4, wherein the weighted summary statistic comprises a sum of N weights respectively assigned to the N sequences by the sequence-to-weight mapping.

6. The system of claim 1, wherein the weighted summary statistic comprises a weighted evolutionary profile.

7. The system of claim 1, wherein the weighted summary statistic comprises a weighted position-specific substitution or conservation frequency.

8. The system of claim 1, wherein the weighted summary statistic comprises a weighted position-specific substitution or conservation score.

9. The system of claim 1, wherein the multiple sequence alignment aligns a query sequence of a first species with a plurality of non-query sequences of a species group that is homologous to the first species.

10. The system of claim 9, wherein weights assigned to non-query sequences in the plurality of non-query sequences are proportional to a degree of homology between the first species and species in the species group.

11. The system of claim 10, wherein the degree of homology is measured by an evolutionary distance between the first species and the species in the species group.

12. The system of claim 11, wherein the degree of homology is measured by a number of mismatches between the query sequence and the non-query sequences.

13. The system of claim 9, wherein those species in the species group that are evolutionarily proximate to the first species are assigned greater weights than those species in the species group that are evolutionarily distant from the first species.

14. The system of claim 13, wherein the greater weights cause the species in the species group that are evolutionarily proximate to the first species to contribute more to the weighted summary statistic than the species in the species group that are evolutionarily distant from the first species.

15. The system of claim 9, wherein the query sequence is assigned a maximum weight.

16. The system of claim 1, further comprising instructions that, when executed by the at least one processor, cause the system to determine the weighted summary statistic by utilizing one or more layers of a machine-learning model.

17. The system of claim 1, further comprising instructions that, when executed by the at least one processor, cause the system to generate the phenotype prediction by utilizing one or more layers of a machine-learning model.

18. The system of claim 17, wherein the one or more layers of the machine-learning model is used as a proxy for a weighted contribution of a non-query sequence to an evolutionary constraint of a variant residue in a query sequence.

19. The system of claim 17, wherein the respective weights are differentiable and learned during a training of the one or more layers of the machine-learning model.

20. The system of claim 19, wherein the respective weights are implemented as part of respective convolution filters that are assigned to each non-query sequence and are learned during the training of the one or more layers of the machine-learning model.

21. The system of claim 1, wherein the sequence-to-weight mapping assigns a plurality of weight sets to a given sequence in the multiple sequence alignment.

22. The system of claim 21, wherein weight sets in the plurality of weight sets are separately applied to generate a plurality of weighted summary statistics for the given sequence.

23. The system of claim 22, wherein the plurality of weight sets is implemented as part of a plurality of convolution filters that is assigned to the given sequence and is learned during a training of one or more layers of a machine-learning model.

24. The system of claim 23, wherein convolution filters in the plurality of convolution filters are applied within one or more additional layers of the machine-learning model as a convolutional layer.

25. The system of claim 23, wherein convolution filters in the plurality of convolution filters are interspersed with activation functions, and stacked across multiple convolution layers.

26. A computer-implemented method comprising:

accessing a sequence-to-weight mapping stored in memory, wherein the sequence-to-weight mapping assigns respective weights to each non-query sequence in a multiple sequence alignment;

based on the sequence-to-weight mapping, determining a weighted summary statistic for a given nucleotide residue category or a given amino acid residue category at a given position in the multiple sequence alignment, based on the respective weights for each non-query sequence in the multiple sequence alignment that has a nucleotide residue of the given nucleotide residue category at the given position; and generating a phenotype prediction for the given position based on the weighted summary statistic.

* * * * *